United States Patent [19]

Hayes

[11] 4,395,563

[45] Jul. 26, 1983

[54] HYDROLYSIS OF ALKOXYSILANES

[75] Inventor: Susan E. Hayes, Schenectady, N.Y.

[73] Assignee: General Electric Company, Waterford, N.Y.

[21] Appl. No.: 316,241

[22] Filed: Oct. 29, 1981

[51] Int. Cl.$^3$ ............................ C07F 7/08; C07F 7/18
[52] U.S. Cl. ................................... 556/459; 556/450; 556/457; 556/463; 556/458; 556/453; 556/455; 556/456
[58] Field of Search ................ 556/450, 459, 457, 463

[56] References Cited

U.S. PATENT DOCUMENTS

| | | | |
|---|---|---|---|
| 2,384,384 | 9/1945 | McGregor et al. | 556/459 |
| 2,415,389 | 2/1947 | Hunter et al. | 556/457 |
| 2,600,307 | 6/1952 | Lucas et al. | 556/459 |
| 2,717,258 | 9/1955 | Kantor | 528/14 |
| 2,827,474 | 3/1958 | Kress | 556/459 |
| 2,832,794 | 4/1958 | Gordon | 556/459 |
| 3,132,167 | 5/1964 | boot et al. | 556/459 |
| 3,262,830 | 7/1966 | Vincent | 556/459 |
| 3,304,318 | 2/1967 | Brady | 556/456 |
| 3,309,390 | 3/1967 | Omietanski | 556/459 |
| 3,364,246 | 1/1968 | Rossmy | 556/459 |
| 3,373,138 | 3/1968 | Brown | 556/459 |
| 3,383,355 | 5/1968 | Cooper | 528/14 |
| 3,642,693 | 2/1972 | Jasinski | 528/14 |
| 3,903,047 | 9/1975 | Ashby | 528/12 |
| 3,939,195 | 2/1976 | Lucking et al. | 556/459 |
| 4,032,557 | 6/1977 | Spork et al. | 556/459 |
| 4,066,680 | 1/1978 | Lewis et al. | 556/442 |
| 4,242,486 | 12/1980 | August et al. | 528/14 |
| 4,321,401 | 3/1982 | Nestler et al. | 556/457 |

OTHER PUBLICATIONS

W. T. Grubb, J. Am. Chem. Soc. 76, 3408-3414, (1954):

A Rate Study of the Silanol Condensation Reaction at 25° in Alcoholic Solvents.
S. W. Kantor, J. Am. Chem. Soc. 75, 2712-2714, (1953); The Hydrolysis of Methoxysilanes. Dimethylsilanediol.

*Primary Examiner*—Paul F. Shaver

[57] ABSTRACT

Alkoxysilanes are hydrolyzed with water in the presence of various hydrolysis catalysts. The hydrolysis catalysts include the solid oxides of the Group IIa metals and solid acid catalysts. The solid acid catalysts are used in conjunction with neutralizing agents and optionally with condensation catalysts.

Generally, the process for hydrolyzing alkoxysilanes comprises: mixing an alkoxysilane, a stoichiometric excess of water and an effective catalytic amount of hydrolysis catalyst selected from the group consisting of a solid oxide of a Group IIa metal, a solid acid catalyst and mixtures thereof; neutralizing the hydrolysis mixture with a sufficient amount of neutralizing agent, for example, magnesium oxide; and separating the hydrolysis product from the mixture. When a Group IIa metal oxide hydrolysis catalyst is used, the liquid portion of the hydrolysate is neutral, and no additional neutralizing agent is required in the mixture.

By the process of the present invention, the average chain length of silanol-stopped polysiloxanes can be controlled. A stabilized, crystalline tetramethyldisiloxane diol and a crystalline dimethyldisilanol have also been prepared by modified catalytic hydrolysis processes using solid acid catalysts to catalyze the hydrolysis of dimethyldimethoxysilane with water.

81 Claims, No Drawings

HYDROLYSIS OF ALKOXYSILANES

BACKGROUND OF THE INVENTION

This invention relates to processes for the hydrolysis of alkoxy-functional silanes, and more particularly, to methods for the catalytic hydrolysis of alkoxysilanes.

Low molecular weight, silanol-stopped (hydroxyend blocked) linear diorganopolysiloxanes are well-known materials in the organosilicon art. One well-known commercially available material is a low molecular weight, silanol-stopped dimethylpolysiloxane fluid which has a variety of utilities including use as a rubber processing aid, used in silicone hard coats, paper release coatings, release emulsions and room temperature vulcanizable silicone rubbers.

The silanol-stopped diorganopolysiloxane fluids have been prepared, for example, by the carefully controlled hydrolysis of diorganodihalosilanes, by neutralization of metal ester and blocked linear diorganosiloxanes, by reaction of diorganopolysiloxanes with water and an organic nitrile in the presence of a basic catalyst, by reaction of diorganopolysiloxanes with aqueous solutions of monobasic acids, by the hydrolysis of trimers, such as hexamethylcyclotrisiloxane catalyzed with an acid clay catalyst as described in U.S. Pat. No. 3,309,390, and the like. The prior art also teaches the water hydrolysis of dialkyldialkoxysilanes with excess water heated at the boiling point using rigorously neutral conditions, and acid catalysts have been used for the hydrolysis of dialkyldialkoxysilanes for making higher molecular weight polymeric silicones as disclosed in U.S. Pat. No. 2,384,384. Alkoxysilanes have also been hydrolyzed using strongly acidic cation exchange resins as the hydrolysis catalyst as disclosed in U.S. Pat. No. 3,304,318.

Generally, it has been difficult to hydrolyze diorgano di-functional silanes, such as dialkyldichlorosilanes or dialkyldialkoxysilanes, to produce low molecular weight, linear silanol-stopped diorganopolysiloxane fluids free of cyclic compounds. Most of the prior art methods discussed above result in mixtures of the desired materials with high molecular weight linear polysiloxanediols or polysiloxane cyclics or both. It is very difficult or impossible to separate the desired materials from these high molecular weight and cyclic components. Furthermore, many of the prior art processes, wherein the silanol-stopped polysiloxanes are made from dialkoxysilanes, produce oligomers having a high alkoxy content, that is, may of the end groups of the polymers are endcapped with alkoxy groups. It has also been difficult to prepare low molecular weight silanol-stopped polysiloxanes having controlled chain lengths by prior art catalyst hydrolysis processes.

Trifunctional alkoxysilanes, RSi(OR')$_3$, wherein R is methyl or phenyl, have been hydrolyzed by a process described in U.S. Pat. No. 3,642,693. The hydrolysis process of the trialkoxysilanes is carried out under weakly basic conditions using saturated aqueous solutions of barium hydroxide, calcium hydroxide and strontium hydroxide prepared from the corresponding Group IIa metal oxides and water. There appears to be no reference or suggestion in U.S. Pat. No. 3,642,693 of the hydrolysis of the dialkoxysilanes or of the formation of low molecular weight silanol-stopped diorganopolysiloxane fluids substantially free of cyclic compounds.

In J. Am. Chem. Soc. 76, 3408–3414 (1954), the rates of silanol condensation reactions in methanol with both acidic and basic catalysis are measured. However, even though the condensation reaction of

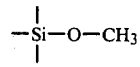

groups with

groups is described, it appears that the method has not been used to reduce the alkoxy content of a siloxane made from alkoxysilane. Generally, polysiloxane silanols have been made from alkoxysilanes using a moderate excess of water in a one-step hydrolysis, and it appears that except for U.S. Pat. No. 4,032,557, there has been no attempt to reduce the alkoxy levels below the resulting equilibrium value of about 1 to about 3%. U.S. Pat. No. 4,032,557, describes steam distillation in the presense of chlorosilanes to reduce the residual methoxy chain stopping from 2% to 0.3% of the chain ends.

Accordingly, it is an object of the present invention to provide a process for the catalytic hydrolysis of alkoxysilanes.

It is another object of the present invention to provide a process for the catalytic hydrolysis of alkoxysilanes, including diorganodialkoxysilanes, which results in a high yield of low molecular weight, linear polysiloxane diols which have little or no cyclic by-products.

Another object of the present invention is to provide a process for the catalytic hydrolysis of diorganodialkoxysilanes wherein the diorganodialkoxysilane is extensively converted to silanol end-stopped oligomers averaging about 2 to about 8 siloxane units.

It is also an object of the present invention to provide a process for preparing silanol-stopped, linear polysiloxanes from alkoxysilanes, e.g., dialkoxysilanes, wherein the alkoxy content of the product is substantially reduced.

Another object of the present invention is to provide a method for controlling the chain length of low molecular weight, linear, silanol-stopped polysiloxanes made by the catalytic hydrolysis of alkoxysilanes, such as, dialkoxysilanes.

Another object of the present invention is to provide a simplified process for preparing and isolating silanol-stopped, low molecular weight, linear polysiloxanes, thereby eliminating the complex separation techniques necessitated by many of the prior art methods.

Still another object of the present invention is to provide stabilized crystalline tetramethyldisiloxanediol and dimethyldisiloxanediol prepared by the catalytic hydrolysis of dimethyldimethoxysilane.

Other objects and advantages of the present invention will become apparent from the following detailed description.

SUMMARY OF THE INVENTION

The objects and advantages of this invention are realized by the catalytic hydrolysis of alkoxysilanes having the general formula:

$$(R'O)_a SiR_{4-a}$$

wherein R is selected from the group consisting of alkyl, haloalkyl, cycloalkyl, aryl, arylalkyl, alkaryl, alkenyl, hydrogen and mixtures thereof; R' is alkyl; and a is an integer from 1 to 4. The catalytic hydrolyses of the present invention may be carried out with various catalysts and combinations of catalysts. The catalysts include the oxides of the Group IIa metals of the Periodic Chart of the elements, generally referred to herein as the Group IIa metal oxide catalysts, and solid acid catalysts which may be used in conjunction with a neutralization agent, such as magnesium oxide or Fuller's earth, or a neutralization agent and a condensation catalyst, such as magnesium oxide and calcium oxide respectively.

Generally, the process for hydrolyzing the alkoxysilanes comprises mixing an alkoxysilane, a stoichiometric excess of water and an effective catalytic amount of solid hydrolysis catalyst selected from the group consisting of a solid oxide of a Group IIa metal and a solid acid catalyst to form a hydrolysis mixture of hydrolyzed alkoxysilane, reaction by-products, hydrolysis catalyst and unreacted water; separating volatile by-products and unreacted reagents from the hydrolyzed alkoxysilane in the presence of the catalyst to form a devolatilized hydrolysis mixture, said separation being one which reduces the alkoxy content of the alkoxysilane; neutralizing the devolatilized hydrolysis mixture with a suitable amount of neutralizing agent when the catalyst is a solid acid catalyst; optionally, adding a suitable amount of condensation catalyst to increase the molecular weight of the hydrolysis product; and separating the solid hydrolysis catalyst from the product. When the solid oxides of Group IIa metals of the Periodic Chart of the Elements are used as hydrolysis catalysts, the separated hydrolysis product is essentially neutral, and it is not necessary to add a neutralizing agent thereto. The Group IIa metal oxides also serve as condensation catalysts to condense the hydroxy terminated silanes, and therefore, the addition of condensation catalyst is optional. As used herein, a neutralized hydrolysis mixture has a pH at or near 7. In those embodiments wherein a solid acid catalyst is used, the devolatilization step of the process, that is, the separation of volatile by-products and unreacted reagents from the hydrolyzed alkoxy-silane, is particularly effective in reducing the alkoxy content of the alkoxysilane, and in those embodiments wherein the Group IIa metal oxide solid catalysts are used, the devolatilization step of the process is less effective, and sometimes has no effect, in reducing the alkoxy content.

In accordance with the present invention, it has also been discovered that by using different hydrolysis catalysts or combinations thereof, the chain length of the silanol-stopped polysiloxane products can be controlled, and low molecular weight, linear, silanol-stopped polysiloxanes having average chain lengths of about 2 to about 3 siloxane units, of about 4 to about 6 siloxane units or higher can be prepared by varying the metal oxide of the Group IIa metals of the Periodic Chart of the Elements when they are used either as the hydrolysis catalyst, or optionally, as the neutralization or condensation agent for a solid acid hydrolysis catalyst in the catalytic hydrolysis of alkoxysilanes.

Stable, crystalline tetramethyldisiloxane diol has also been prepared by the process of the present invention by hydrolyzing dimethyldimethoxysilane with water at temperatures less than about 25° C. in the presence of a solid acid catalyst and solid magnesium oxide catalyst. It has been observed that the tetramethyldisiloxanediol crystallized from the fluids made by the process of the present invention remained stable for several months even though there was no recrystallization of the product. The stability of this crystal compound to further silanol condensation upon standing was unexpected, and it is concluded that the process of the present invention substantially increases the stability of the tetramethyldisiloxanediol.

It has also been discovered that crystalline dimethyldisilanol can be made by the process of the present invention by hydrolyzing dimethyldimethoxysilane with water at temperatures less than about 5° C. in the presence of a solid acid catalyst. Furthermore, by the process of the present invention, the alkoxy content of polysiloxanes made from alkoxysilanes has been substantially reduced or eliminated. It has also been found that substantially no cyclic siloxanes are formed by the process of the present invention.

DETAILED DESCRIPTION OF THE INVENTION

In the general process of the invention wherein alkoxysilanes are mixed with an excess of water in the presence of an effective catalytic amount of a solid hydrolysis catalyst selected from the group consisting of a solid oxide of a Group IIa metal and a solid acid catalyst to form a hydrolysis mixture which is then devolatilized while separating volatile by-products and volatile, unreacted components from the hydrolysis mixture in the presence of the solid catalyst which thereby further dealkoxylates, that is, reduces the alkoxy content, neutralized with a neutralizing agent, optionally condensed, and the hydrolyzed and condensed siloxanediols separated therefrom, no neutralizing agent is required when the hydrolysis catalyst is a Group IIa metal oxide because the separated siloxanediols are already neutral. Furthermore, when the Group IIa metal oxides are used as the solid hydrolysis catalyst, condensation of silanol-stopped silanes occurs during the hydrolysis to form silanol-stopped polysiloxanes. Alternatively stated, the hydrolysis catalyst is sufficiently insoluble in the hydrolysate after separation of the water that the liquid portion of the hydrolysate is essentially neutral. Nonetheless, the oxides are active as condensation catalysts in the water-containing or water-free hydrolysate.

When a solid acid catalyst is used as solid hydrolysis catalyst, it usually introduces a small amount of soluble acid which must be neutalized with a separate neutralizing agent. Of course, if none of the solid acid catalyst is soluble, then neutralization is not necessary. In preferred embodiments, the neutralizing agent is either magnesium oxide or magnesium oxide and a separate addition of calcium oxide because these and other Group IIa metal oxides neutralize the polysiloxanediol and also increase the molecular weight of the polysiloxanediol to specific desired values without catalyzing the formation of cyclic polysiloxane by-products. Naturally, mixtures of the foregoing agents may also be used in the process. Although calcium oxide may be used alone as the neutralizing agent when solid acid catalyst, preferably an acid activated clay, is used as hydrolysis catalyst, the linear, low molecular weight polysiloxane condensation products are difficult to neutralize. Insufficiently neutralized products are not stable and further condensation occurs within the product upon standing. Separation of the product from the hydrolysis mixtures and preferred reaction conditions are discussed in more detail below.

In its broadest aspects, the processes of the present invention can be used to produce polysiloxanesilanols from any type of alkoxysilane or mixtures thereof. The solid catalysts may be used for the catalytic hydrolysis of alkoxysilanes having the general formula:

$$(R'O)_a SiR_{4-a}$$

wherein R', R and a are defined above. Thus, the process of the present invention may be used to produce polysiloxanesilanols from monoalkoxysilanes, dialkoxysilanes, trialkoxysilanes, tetraalkoxysilanes and mixtures thereof.

The preferred alkoxysilane hydrolyzates which are within the scope of this invention, are di-functional alkoxy silanes, that is, the silane has only two alkoxy groups. The other two positions upon the silicon atom may contain hydrocarbon radicals which form a silicon to carbon bond and which do not cause excessive cross-linking under the selected reaction conditions, or they may contain hydrogen atoms connected to the silicon atom by a hydrogensilicon bond, or they may contain a hydrocarbon radical which forms a silicon to carbon bond, and a hydrogen atom which forms a silicon to hydrogen bond, or combinations of the foregoing. Thus, preferred individual dialkoxysilanes which can be employed, are those having the general formula:

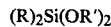
$$(R)_2 Si(OR')_2$$

wherein R is selected from the group consisting of alkyl, fluoroalkyl, cycloalkyl, aryl, arylalkyl, alkaryl, alkenyl, hydrogen and mixtures thereof, and R' is alkyl. In preferred embodiments, the dialkoxysilanes are those diorganodialkoxysilanes selected from the group consisting of dialkyldialkoxysilane, diaryldialkoxysilane and alkylalkenyldialkoxysilane. Corresponding monoorganodialkoxysilanes having a hydrogen atom substituted upon the silicon atom may also be used in the process of the present invention. Mixtures or any combination of the foregoing types of dialkoxysilanes can be employed. Materials useful as rubber processing aids are linear, and therefore, they are produced from the dialkoxysilanes having the formula $R_2Si(OR')_2$.

In most embodiments, when R is alkyl, the alkyl group comprises 1 to about 10 carbon atoms, for example, methyl, ethyl, propyl, pentyl, hexyl, octyl and the like. In those embodiments wherein R is aryl, the aryl group generally comprises about 6 to about 20 carbon atoms, for example, phenyl, biphenyl, naphthyl, and anthryl. Alkaryl groups include xylyl and tolyl, and aralkyl groups include benzyl. In those embodiments where R is alkenyl, the alkenyl preferably comprises about 2 to about 10 carbon atoms, for example, vinyl, allyl, butadienyl, and the like. Alkylaryldialkoxysilanes, alkylalkenyldialkoxysilanes, arylalkenyldialkoxysilanes, and the like, are also within the scope of the present invention.

The alkoxy groups upon the alkoxysilanes may be the same or different. In preferred embodiments, the two alkoxy groups upon the silicon atom connected to the silicon atom by an oxygen-silicon bond, have 1 to about 10 carbon atoms and include methoxy, ethoxy, propoxy, butoxy, pentoxy, and the like. Naturally, in all of the foregoing hydrocarbon radicals upon the dialkoxysilanes, substituted derivatives of the hydrocarbon radical may be used in the hydrolysis reactions of the present invention as long as they do not react undesirably under the selected reaction conditions.

Specific examples of dialkoxysilanes which are within the scope of the invention, include dimethyldimethoxysilane, dimethyldiethoxysilane, diphenyldimethoxysilane, methylvinyldimethoxysilane, propylvinyldiethoxysilane, divinyldimethoxysilane, methyldimethoxysilane, butyldimethoxysilane, and the like.

The hydrolysis of the alkoxysilanes is carried out by using water. In preferred embodiments, the water is distilled, deionized or otherwise treated to remove or deplete substantially all foreign matter and ions found therein. The water is used in a stoichiometric excess, that is, a sufficient amount to carry out a complete hydrolysis of the alkoxysilane. For example, it is generally preferred to use at least 2 moles of water per mole of alkoxysilane, and generally, it is more preferred to use from about 2 moles to about 6 moles or more water per mole of alkoxysilane.

Although specific embodiments herein describe dialkoxysilanes, it is to be understood that the descriptions also relate to all alkoxysilanes having the general formula described above.

Generally, the catalytic hydrolysis process of the present invention is carried out using a solid Group IIa metal oxide catalyst or a solid acid catalyst used in conjunction with at least one specific solid Group IIa metal oxide, such as, magnesium oxide. The preferred solid Group IIa metal oxide catalysts are magnesium oxide, calcium oxide and barium oxide. Other Group IIa oxide catalysts include strontium oxide and beryllium oxide, however, generally beryllium oxide is avoided because of the poisonous nature of the material.

Halo, as used herein, means fluoro, chloro or bromo.

CATALYTIC HYDROLYSIS OF DIALKOXYSILANES USING SOLID GROUP IIa METAL OXIDE CATALYSTS

In accordance with at least some of the objects of the present invention, the catalytic hydrolysis of dialkoxysilanes comprises:
(a) mixing a dialkoxysilane with a stoichiometric excess of water in the presence of an effective catalytic amount of a solid Group IIa metal oxide catalyst to form a linear, silanol-stopped, low molecular weight polysiloxane and reaction by-products; and
(b) separating the volatile reaction by-products, catalyst and unreacted water from the silanol-stopped polysiloxane product.

In an additional step, the solid catalyst is also separated from the silanol-stopped polysiloxane product. In preferred embodiments, a filter aid is added to the silanol-stopped polysiloxane product, and the medium is filtered to remove solid particles from the fluid. In step (b) the volatile reaction by-products are preferably separated by distillation.

The amount of catalyst in each mode of the invention is not critical as long as there is an effective amount of the solid catalyst to promote the hydrolysis reaction. Thus, in accordance with at least some of the objects of the present invention, an effective catalytic amount of a Group IIa metal oxide catalyst is used to form a silanol-stopped polysiloxane product. Usually, in the case of the Group IIa metal oxide catalyst, an effective amount is at least about 0.01 part by weight of the catalyst per 100 parts by weight of the dialkoxysilane. Since the Group IIa metal oxide catalysts are insoluble in the reaction mixture, there is essentially no upper limit in the amount of catalyst used in the hydrolysis reaction mixture. In preferred embodiments, the amount of Group IIa metal oxide catalyst comprises about 0.01 to about 10 parts by weight of Group IIa metal oxide catalyst per 100 parts by weight of dialkoxysilane, and in more preferred embodiments, the effective catalytic amount of Group IIa metal oxide catalyst comprises about 0.08 to about 1.5 parts by weight of Group IIa metal oxide catalyst per 100 parts by weight of dialkoxysilane.

In accordance with the process of the present invention, there is essentially no upper limit to the amount of catalyst, whether it is the Group IIa metal oxide catalyst, the acid solid catalyst, or the condensation catalysts. Optimum amounts of catalyst material can be determined for each particular dialkoxysilane reactant and the particular reaction conditions and the desired chain length of the product from the teachings of the present invention.

The dialkoxysilane, the stoichiometric excess of water and the solid Group IIa metal oxide catalyst, or the acid solid catalyst discussed below, must be sufficiently mixed to form the silanol-stopped fluids of the invention since the dialkoxysilane, the water, the unhydrolyzed alkoxysilanes and the solid catalyst form three separate phases. Vigorous stirring or mixing of the dialkoxysilane, water and catalyst is recommended for complete mixing of the reactants and catalyst. The mixing or stirring must be sufficient to blend or completely mix the two liquid phases and to disperse the solid, insoluble catalyst throughout the reaction mixture. Any high speed stirrer, blender or other suitable mixer is generally recommended for the mixing of the reactants and the catalyst.

The temperature of the reaction mixture is generally not critical. The hydrolysis and condensation using the Group IIa metal oxide catalyst may be carried out at almost any temperature including temperatures below ambient, at ambient and above ambient. In certain preferred embodiments, it is preferred to carry out the hydrolysis reaction at temperatures of about 10° C. to about 60° C., and more preferably, at temperatures of about 15° C. to about 50° C. Generally, the hydrolysis reaction is initiated at about 25° C., and a gradual exotherm to about 45° C. after 15 minutes is observed. In preferred embodments, the reaction mixture is allowed to return to ambient temperature after the exotherm, and strong mixing is continued for several hours. The hydrolysis may be initiated and maintained at higher temperatures as long as the boiling points of the reactants still present are not exceeded. However, no benefit is derived from higher temperatures, because the percent of silanol-terminated polymer ends is slightly lower while the energy consumption of the process is increased.

Generally, the length of time that the hydrolysis reaction is carried out, that is, that the dialkoxysilane, the stoichiometric excess of water and the solid Group IIa metal oxide catalyst, are mixed, is not critical as long as there is a sufficient amount of time to form the silanol-stopped polysiloxane fluid. This can be determined when the volatile portion of the reaction mixture is substantially depleted of alkoxy-stopped silanes and silane derivatives, or when the reaction mixture shows no further decrease in the amount of alkoxy endcapping. Determination of the presence of alkoxysilanes in the volatile portion of the reaction mixture can be made using gas-liquid chromatography (GLC). The hydrolysis mixture itself can be analyzed if the reactive protons present such as those in silanols, alcohols and water, are removed by derivatization with an excess of a silyation agent, such as, bis-trimethylsilylacetamide or bis-trimethylsilyltrifluoroacetamide. Such treatment quenches silanol hydrolysis and condensation reactions and allows gas liquid chromatography analysis for the species present both during the process and also in the finished product. Typically, the dialkoxysilane, water and metal oxide catalyst are mixed for about 10 minutes to about 24 hours to obtain substantially complete hydrolysis of the dialkoxysilane. Generally, as defined herein, substantially complete hydrolysis is reached when there are less than about 5% alkoxy groups remaining in the reaction mixture. One skilled in the art can select the reaction time to provide the desired yield and/or the desired amount of hydrolysis and condensation.

In the catalytic hydrolysis of dialkoxysilanes wherein the dialkoxysilane is hydrolyzed with water in the presence of a solid Group IIa metal oxide catalyst, first the volatile portions, fractions or ingredients and then the solids, such as the catalyst, in the reaction mixture are separated from the silanol-stopped polysiloxane fluid. The volatile components generally comprise various reaction by-products, such as alcohols, and unreacted water. For example, in the case of the hydrolysis of dimethyldimethoxysilane with water in the presence of magnesium oxide, the volatile components which are removed from the reaction mixture, are methyl alcohol and water. After all of the volatile materials have been removed by distillation, vacuum distillation or conventional stripping, the product may be subjected to reduced pressure optionally at elevated temperatures to ensure removal of the volatile components. For example, the silanol-stopped dimethylpolysiloxane product may be held at about 40° C. to about 60° C. at a pressure less than atmospheric pressure, for example, about 5 mm Hg to about 760 mm Hg pressure, for about 5 minutes to about 2 hours.

One of the preferred methods of separating the volatile reaction by-products and unreacted water is by distillation or stripping either at reduced pressure, or at elevated temperatures or at elevated temperatures and reduced pressure. The stripping of the volatile components may be carried out, for example, at 15° C. to about 60° C. or higher at atmospheric pressure or, more preferably, at reduced pressure, such as about 5 mm Hg pressure to about 760 mm Hg pressure for about 5 minutes to about 60 minutes to remove the the volatile materials from the mixture.

In the hydrolysis of dialkoxysilanes with Group IIa metal oxide catalyst, the solid Group IIa metal oxide may be removed from the reaction mixture at any time after substantial completion of the hydrolysis. In preferred embodiments, after the volatile components have been separated from the silanol-stopped polysiloxane fluid, the solids in the reaction mixture, such as the Group IIa metal oxide catalyst, are removed or separated from the fluid by any suitable means, for example, by filtration, and a filter aid may be added to the fluid followed by filtration to remove the solid components from the product. Any suitable filter aid or mixtures of filter aids may be used to promote the filtration of solid materials from the fluid product, including, for example, diatomaceous earth, porous colloidal aluminum silicate or other clays which have high natural adsorptive power, and the like. In certain instances, filter aids having neutralizing properties, or filter aids which adjust the pH of the fluid, may be used to obtain desired pH levels in the filtrate.

The polysiloxane fluids formed by the catalytic hydrolysis of the dialkoxysilanes with water in the presence of solid Group IIa metal oxide catalyst, are linear, silanol-stopped polysiloxane, and it has been found in accordance with the present process that the chain length of the silanol-stopped polysiloxanes varies depending upon the particular Group IIa metal oxide catalyst chosen for the catalytic hydrolysis. By chain length of the silanolstopped polysiloxane is meant the number of recurring siloxane

units in the polymer molecule. It has been discovered in accordance with one aspect of the present invention, that the linear, silanol-stopped polysiloxane fluid has a shorter chain length when magnesium oxide is used as catalyst, an intermediate chain length when calcium oxide is used as catalyst, and a higher chain length when barium oxide is used as catalyst. When magnesium oxide is used as the catalyst, it has been found that the linear, low molecular weight, silanolstopped polysiloxane product has an average chain length of about 2 to about 3 siloxane

units. When calcium oxide is used as the catalyst in the hydrolysis reaction, the chain length of the linear, low molecular weight silanol-stopped polysiloxane product has an average of about 5 to about 6 siloxane

units. When barium oxide is used as a hydrolysis catalyst, it has been discovered that the linear silanol-stopped polysiloxane product has a substantially higher viscosity in a range which typically corresponds to about 400 to 500 siloxane —Si(CH$_3$)$_2$O— units. Thus, in accordance with one aspect of the present invention, a method for controlling the chain length of silanol-stopped polysiloxanes prepared by the catalytic hydrolysis of dialkoxysilanes comprising using different metal oxide catalysts from the Group IIa metals of the Periodic Chart of the Elements, has been discovered.

Thus, there is provided a method for controlling the chain length of silanol-stopped polysiloxane prepared by the catalytic hydrolysis of dialkoxysilanes comprising:

(a) mixing an effective catalytic amount of a Group IIa metal oxide catalyst selected from the class consisting of magnesium oxide, calcium oxide and barium oxide with a dialkoxysilane and a stoichiometric excess of water to form a linear, silanol-stopped polysiloxane and reaction byproducts; and (b) separating volatile reaction byproducts and unreacted water from the silanolstopped polysiloxane product, whereby the average polymer chain length varies according to the specific metal oxide catalyst, the silanolstopped polysiloxane having a shorter average chain length when magnesium oxide is used as catalyst, an intermediate average chain length when calcium oxide is used as catalyst and a longer average chain length when barium oxide is used as catalyst. As used herein, the chain length is the number of recurring siloxane (—Si(R)$_2$O—) units, and the shorter chain length generally represents an average of about 2 to about 3 siloxane (—Si(R)$_2$O—); the intermediate chain length is generally an average of about 4 to about 7 recurring siloxane (—Si(R)$_2$O—) units; and higher chain lengths are generally an average of greater than 20 recurring siloxane (—Si(R)$_2$O—) units.

In preferred embodiments, the chain length of linear, silanol-stopped dialkylpolysiloxanes may be varied or controlled by the catalytic hydrolysis of dialkyldialkoxy-silanes comprising:

(a) mixing a Group IIa metal oxide catalyst selected form the class consisting of magnesium oxide, calcium oxide and barium oxide with a dialkyldialkoxysilane and from about 2 to about 6 moles of water per mole of dialkyldialkoxysilane at about 10° C. to about 60° C., the catalyst being used in an amount from about 0.01 part by weight to about 1.5 parts by weight of metal oxide catalyst per 100 parts by weight of dialkyldialkoxysilane;

(b) distilling the reaction mixture after vigorously mixing for about 10 minutes to about 24 hours to separate volatile components including water, from the silanolstopped dialkoxypolysiloxane product; and (c) adding a solid filter medium (filter aid), for example, a porous colloidal aluminum silicate (clay) having high adsorptive power, to the silanol-stopped dialkoxypolysiloxane product and filtering said product, whereby the polymer chain length varies according to the specific metal oxide catalyst, the silanol-stopped dialkylpolysiloxane having an average chain length of about 2 to about 3 siloxane units when magnesium oxide is used as catalyst, an average chain length of about 4 to about 6 siloxane units when calcium oxide is used as catalyst, and a longer average chain length of about 400 to 500 siloxane units, when barium oxide is used as catalyst.

Typical silanol-stopped dialkylpolysiloxanes formed by the process in at least one aspect of the invention, are mixtures in various proportions of hexamethyltrisiloxane-1,5-diol having 3 siloxane units, octamethyltetrasiloxane-1,7-diol having 4 siloxane units and decamethylpentasiloxane-1,9-diol having 5 siloxane units.

CATALYTIC HYDROLYSIS OF ALKOXYSILANES USING SOLID ACID CATALYSTS AND NEUTRALIZATION AND CONDENSATION AGENTS

In those aspects of the present invention wherein the hydrolysis of alkoxysilanes are carried out with a solid acid catalyst used in conjunction with neutralizing and condensing agents, for example, with magnesium oxide and, optionally, calcium oxide, the silanol-stopped polysiloxanes prepared thereby are of such high purity that even those of very short chain length retain their stability for substantially long periods of time. By high purity is meant that the product contains no ionic species or other contaminants which contribute to further condensation over prolonged periods of time.

In this aspect of the invention, the process for the catalytic hydrolysis of alkoxysilanes comprises:

(a) mixing an alkoxysilane with a stoichiometric excess of water in the presence of an effective catalytic amount of solid acid catalyst to initiate hydrolysis of the alkoxysilane and thereby form a mixture comprising partially hydrolyzed alkoxysilane, solid acid catalyst, water and reaction by-products;

(b) separating the volatile reaction by-products and unreacted water from the partially hydrolyzed silane in the presence of the solid and catalyst whereby the solid acid catalyst catalyzes a further reduction in the number of alkoxy groups present by catalyzing the condensation of the alkoxysilane species and the silanol species to form devolatilized alkoxysilane-reduced or -depleted hydrolyzate;

(c) neutralizing the devolatilized alkoxysilane-reduced or -depleted hydrolysate with a suitable solid neutralizing agent, thereby obtaining a neutralized, low molecular weight, linear, silanol-stopped polysiloxane and condensation by-products;

(d) optionally adding a solid condensation catalyst to the neutralized polysiloxane to increase the chain length of the polysiloxane; and (e) separating the volatile by-products and solid catalyst from the low molecular weight, linear, silanol-stopped polysiloxane.

In this aspect of the present invention, it has been discovered that linear, low molecular weight silanol-stopped polysiloxane products can be prepared from dialkoxysilanes by using a solid acid catalyst in conjunction with neutralizing and condensing agents, such as, for example, a Group IIa metal oxide catalyst or catalysts. For example, in one preferred embodiment, a solid acid catalyst is used in conjunction with magnesium oxide and calcium oxide to obtain linear, low molecular weight silanol-stopped polysiloxane product from dialkoxysilanes.

Almost any acid catalyst which is solid and which remains solid during the hydrolysis reaction, may be used as the solid acid catalyst. For example, one preferred type of solid acid catalyst is an acid-activated clay identified as FILTROL, a trademark of Filtrol Corporation. Another type of solid acid catalysts are the acidic cation exchange resins. Strongly acidic cation exchange resins are described in U.S. Pat. No. 3,304,318. The solid acid catalyst is generally defined as a solid having active protons on its surface, or, alternatively stated, a catalyst which is insoluble throughout the process and has active hydrogen atom on it. Such catalysts are well-known in the art and may be any solid which has absorbed on it or which has been treated with an acid, preferably an acid of a pH below 5. As used herein, a solid acid catalyst does not include a liquid acid catalyst or a solid, pure acid catalyst which becomes soluble at any point in the process. As explained above, the preferred catalysts are aluminum silicate clays activated with a mineral acid, such as sulfuric acid or hydrochloric acid which are available commercially as various grades of FILTROL through the Filtrol Corporation, Los Angeles, CA. Various solid acid catalysts are described in U.S. Pat. No. 3,903,047, U.S. Pat. No. 3,853,934 and U.S. Pat. No. 3,398,177. As expressed above, in accordance with at least some of the objects of the present invention, it is critical to combine either the solid acid catalyst with a neutralizing and condensation catalyst, such as the Group II metal oxide, or to wash or otherwise pretreat the solid acid catalyst so that it does not contain traces of soluble acid to achieve the highly stable polysiloxane products having little or no cyclic siloxanes therein.

As explained above, the dialkoxysilane is vigorously mixed with a stoichiometric excess of water in the presence of an effective catalytic amount of solid acid catalyst to initiate the hydrolysis and form a hydrolysis mixture which contains partially hydrolyzed alkoxysilane, solid acid catalyst, water and reaction by-products which are volatile. An effective catalytic amount of acid solid catalyst is generally at least about 0.01 part by weight of catalyst per 100 parts by weight of dialkoxysilane, and preferably the solid acid catalyst is present in an amount of about 0.01 to about 20 parts by weight per 100 parts by weight of dialkoxysilane. In the most preferred embodiments, the solid acid catalyst is used in an amount of about 0.5 to about 2.0 parts by weight per 100 parts by weight of dialkoxysilane.

The volatile reaction by-products and unreacted water are separated from the silanol-stopped polysiloxane fluid in the presence of the solid acid catalyst, preferably by distillation. The distillation or stripping may be at any temperature below ambient or above ambient and at reduced pressure as discussed above. In preferred embodiments the stripping is carried out at temperatures between about 15° C. to about 40° C. at reduced pressures no greater than about 20 mm Hg pressure.

It has been found that generally the initial hydrolysis removed 93% to 95% of the alkoxy end groups of the dialkoxysilane when the solid acid catalyst is used as hydrolysis catalyst. After the separation step, that is, after the distillation or stripping of most of the reaction by-products and water, the alkoxy elimination continues by the condensation of alkoxy groups with silanol groups and ultimately produces a silanol having about 99.9% silanol end groups. At this point, hydrolysis is substantially complete. As explained above, the hydrolysis activity can be monitored as desired by any suitable technique including gas-liquid chromatography. The length of time of the reaction depends upon several variables including reactants, reaction vessels and equipment, concentration of reactants and catalysts and the like. The reaction can be monitored by gas-liquid chromatography so that the hydrolysis can be terminated before undesirable by-products, for example, cyclic polysiloxanes, being to form and/or accumulate in the reaction mixture.

After the volatile reaction by-products and unreacted water have been removed by vacuum distillation or other suitable stripping technique, magnesium oxide condensation catalyst and neutralization agent is added to the silanol-stopped polysiloxane to neutralize any soluble acid from the solid acid catalyst promoting stabilization of the product from further condensation and further condensing the hydrolysate to a silanol-stopped polysiloxane product having an average chain length of about 3 to about 4 recurring siloxane units. Generally, the solid neutralization agent (magnesium oxide) may be added in any effective amount to neutralize the medium which can embrace an amount as low as about 0.05 part by weight of neutralizing agent per each part by weight of solid acid catalyst. Although there is essentially no upper limit to the amount of solid neutralizing agent (magnesium oxide) which can be added to the mixture both as neutralization agent and condensation agent or catalyst, up to 6 parts by weight or more of the neutralizing agent per 1 part by weight of solid acid catalyst is preferably used in the mixture.

It has been discovered that the solid acid catalyst/magnesium oxide system is a unique hydrolysis system in that the hydrolysis is rapid, and there is very little subsequent condensation of the product resulting in an unusually stable product.

To synthesize a silanol-stopped polysiloxane fluid having an average chain-length of about 5 to about 6 recurring siloxane (—Si(R)$_2$)O—) units, a solid condensation catalyst, for example, calcium oxide condensation catalyst, may be added to the neutralized silanol-stopped polysiloxane fluid prepared by adding a neutralization agent (magnesium oxide) to the reaction mixture. The amount of condensation catalyst is not critical as long as there is an effective amount to provide the desired condensation during this optional step. An effective catalytic amount of the condensation catalyst is generally at least about 0.05 part by weight of condensation catalyst per 1.0 part by weight of solid acid catalyst, and preferably, about 0.5 to about 6.0 parts by weight of condensation catalyst per each part by weight of the solid acid catalyst. Greater amounts of condensation catalyst, for example, calcium oxide, may be used in the fluid but with no additional benefit.

When the solid acid catalyst is used to initiate the hydrolysis of the dialkoxysilane with water, the reaction may be carried out at any temperature. It is preferably initiated at or below ambient temperature, that is, about 0° C. to about 25° C., either by external cooling of the mixture or by using ice as part of the hydrolyzing water. Thereafter, the temperature may be maintained within about 0° C. to about 25° C., or it may be increased by the heat provided from the exothermic reaction temperature provided by the reaction or it may be heated. The exothermic reaction generally elevates the temperature by 25° to 35° C., and additional heat may be externally supplied to maintain the temperature between about 30° C. and about 50° C. after the exothermic reaction ceases. It is also within the scope of at least some of the objects of the present invention to carry out the hydrolysis reactions at temperatures between about 35° C. to about 50° C. or higher, although no benefit is generally obtained by heating the reaction mixture above about 60° C., and higher temperatures promote the formation of cyclic siloxanes.

After the alkoxysilane has been vigorously mixed with water and solid acid catalyst for a sufficient time at appropriate temperatures to form hydrolysis product, the next step in the process is either the addition of the neutralizing agent, or alternatively, filtering the solid acid catalyst from the hydrolysis product mixture before the addition of the neutralizing agent. The final residual alkoxy level is greatly reduced if the volatile components are first removed by vacuum distillation in the presence of the solid acid catalyst. If the solid acid catalyst, such as FILTROL 20, an acid activated clay, is present and not neutralized during the stripping, distillation or vacuum distillation, it catalyzes the condensation of alkoxy groups with silanol groups producing alcohols and siloxane bonds, for example, as follows where methyl alcohol is formed during the reaction:

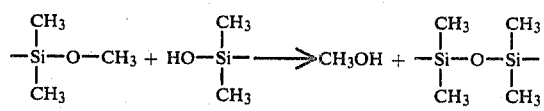

In the most preferred embodiment of the foregoing step in the process carried out in accordance with at least some of the objects of the present invention, alcohol, e.g., methanol, and water are distilled under vacuum using a distillation column of several theoretical plates at 20° C. to 40° C. and at 15 to 40 mm Hg pressure. The distillation column, that is distilling the hydrolysate mixture under vacuum is not necessary, but it improves yield and dealkoxylation. The separation can be carried out by stripping or distilling at lower temperatures and higher pressures than shown above, but the separation under these conditions takes a longer period of time. Furthermore, higher temperatures and lower pressures tend to promote the formation of cyclic polysiloxanes. It is generally recommended that the distillation be terminated as soon as the volatile components are removed from the mixture to minimize the formation of cyclic siloxanes.

The removal of the volatile components from the hydrolysis mixture is also referred to herein as a devolatilization, and it occurs when the reaction mixture resulting from the hydrolysis of the alkoxysilane is distilled. Thus, when the volatile reaction by-products and unreacted water are separated from the partially hydrolyzed silane or the alkoxysilane hydrolyzate, e.g., by distillation, the devolatilization occurs. Furthermore, when the devolatilization occurs in the presence of the solid acid catalyst, alkoxy groups and silanol groups condense to form siloxane bonds and alcohol, the alcohol being removed by the distillation. In this manner the silane diols and/or siloxane diols having a low alkoxy concentration are formed by the process of the present invention.

When the neutralization/condensation catalyst, for example, magnesium oxide, is added to the reaction mixture, the reaction temperature is not critical, and temperatures ranging from below ambient temperature to above ambient temperature may be used. Generally, temperatures between about 10° C. to about 60° C. may be used. When the calcium oxide condensation catalyst is added to the neutralized silanol-stopped polysiloxane fluid to increase the average chain length of the fluid to about 5 or 6 siloxane units, heating of the mixture is optional, and the addition may be carried out, preferably at about 10° C. to about 60° C. The temperature of the addition is not critical, nor is the length of time that the calcium oxide condensation catalyst is mixed with the polysiloxane fluids as long as there is a sufficient time to disperse evenly the solid calcium oxide in the mixture. The calcium oxide condensation catalyst may be mixed with the fluid for about 2 minutes to about 15 minutes or longer up to about 4 hours. No additional benefit is derived from mixing the calcium oxide condensation catalyst with the fluid at elevated temperatures for longer periods. Excessive temperatures for prolonged periods of time lead to the formation of cyclic polysiloxanes.

After the neutralization and condensation reactions, that is, after mixing with magnesium oxide, and optionally, calcium oxide, all volatile components are separated from the silanol-stopped polysiloxane fluid by distillation, and preferably by vacuum distillation. This distillation does not require a column. Although the stripping may be carried out at atmospheric pressure at an elevated temperature, it is generally preferred to distill the volatile materials, including water, from the fluid at about 30° C. to about 50° C. and at about 5 to about 760 mm Hg pressure, and more preferably at about 15 to about 50 mm Hg pressure until all the volatile materials are removed. In an optional step, the fluid is then held at a given temperature, for example, about 10° C. to about 60° C., and more preferably at about 40° C. to about 45° C., at reduced pressure, for example, about 5 to about 760 mm Hg pressure for a short period of time, for example, about 10 to about 20 minutes, to ensure removal of volatile materials.

After the stripping, solid materials are separated from the fluid by any convenient method, for example by filtration. Most of the solids are undissolved catalysts, such as magnesium oxide catalyst, solid acid catalyst and/or calcium oxide catalyst.

Generally, in preferred embodiments, a filter aid is added to the fluid to facilitate filtration of the solids from the silanol-stopped polysiloxane fluid. Adsorptive clays and diatomaceous earth and other adsorptive materials have been discussed above and may be used for this purpose. For example, about 0.05 part to about 1.0 part by weight of a mixture of diatomaceous earth and Fuller's earth (porous colloidal aluminum silicate) per 100 parts of dialkoxysilane may be added as needed. In certain preferred embodiments, the filter aid is added to adjust the alkalinity of the product, for example, if the alkalinity (basicity) is greater than about 5 parts per million KOH, the silanol-stopped polysiloxane fluid product may be treated with additional diatomaceous earth, Fuller's earth, and the like to reduce the alkalinity of the product. An alkaline level greater than about 100 parts per million KOH indicates that the stripping was not complete and the stripping and filtering steps are preferably repeated. Conventional titration methods may be used to determine the amount of acid or base in the silanolstopped polysiloxane fluid, or any other suitable alternative may be used to determine the alkaline or acid level of the product.

In one preferred embodiment of the present invention, catalytic hydrolysis of dialkyldialkoxysilanes comprises:

(a) adding a dialkyldialkoxysilane to a mixture of about 3 to about 6 moles of water per mole of dialkyldialkoxysilane and about 0.5 to about 20 parts by weight of acid activated clay catalyst per 100 parts by weight of dialkyldialkoxysilane at a temperature of about 10° C. to about 25° C.;

(b) mixing vigorously the mixture of step (a) at a temperature between about 10° C. to about 50° C. for the minimum time required to form a single phase from the various phases to about 45 minutes to initiate hydrolysis of the dialkyldialkoxysilane and thereby form a mixture comprising partially hydrolyzed dialkylsilanes, acid solid catalyst, water and reaction by-products;

(c) distilling the mixture at a temperature between about 15° C. and about 50° C. and at reduced pressure no less than about 15 mm Hg. pressure for a suitable length of time in the presence of the unneutralized solid acid catalyst to separate the volatile reaction by-products and water from the partially hydrolyzed dialkylsilane and to condense silanol and alkoxy groups thereby forming low molecular weight, linear dialkylsilane diol product having low alkoxy concentration;

(d) adding about 0.05 to about 6.0 parts by weight solid magnesium oxide neutralizing agent and condensation catalyst per 1.0 part by weight of acid solid catalyst, and stirring for a sufficient time to evenly disperse the solid magnesium oxide, thereby obtaining a mixture containing neutralized, low molecular weight, linear, silanol-stopped dialkyl polysiloxane having an average chain length of about 3 to about 4 siloxane (—Si(R)$_2$O—) units;

(e) optionally adding up to about 6.0 parts by weight solid calcium oxide condensation catalyst per 1.0 part by weight of acid solid catalyst and stirring for a sufficient time to evenly disperse the solid calcium oxide in the mixture, thereby obtaining a mixture containing condensed, low molecular weight, linear, silanol-stopped dialkylpolysiloxane having an average chain length of about 5 to about 6 siloxane (—Si(R)$_2$O—) units;

(f) distilling the mixture containing low molecular weight, linear, silanol-stopped dialkylpolysiloxane preferably at a temperature between about 15° C. and about 50° C. and at a reduced pressure until all volatile materials are removed; and (g) filtering the mixture remaining after removal of volatile materials to remove solid catalysts to obtain low molecular weight linear, silanol-stopped dialkylpolysiloxane product.

When the dialkyldialkoxysilane is dimethyldimethoxysilane, the product obtained by the foregoing process is a dimethylpolysiloxane diol.

When the mixture comprising the hydrolyzate, acid solid catalyst, water, reaction by-products and/or other components is distilled in the presence of solid acid catalyst to separate the volatile reaction by-products and water from the hydrolyzate and to condense silanol and alkoxy groups, the length of time that the distillation is carried out, must be controlled to achieve maximum methoxy reduction without the formation of cyclic polysiloxanes. This is defined herein as a suitable length of time and can be determined by following the analysis of the mixture, for example, by gas-liquid chromatography, or by observing the termination of the removal of the volatile components and the like. Naturally, there are a number of variables which one skilled in the art must consider when determining the suitable length of time for the distillation of the mixture including temperature, pressure, boiling point, components of the mixture, type of distillation equipment and the like.

The solid catalyst/magnesium oxide/calcium oxide system may be used to provide a process for varying the chain length of low molecular weight silanol-stopped polysiloxane fluids from an average of about 2.5 recurring siloxane units to an average of about 6 recurring siloxane units in a short period of time at low temperatures without forming cyclic siloxane condensation products. Thus, in accordance with one aspect of the present invention, there is provided a method for controlling the chain length of low molecular weight, linear, silanol-stopped polysiloxanes prepared by the catalytic hydrolysis of dialkoxysilanes comprising:
(a) mixing a dialkoxysilane with a stoichiometric excess of water in the presence of an effective catalytic amount of solid acid catalyst to initiate hydrolysis of the dialkoxysilane and thereby form a mixture comprising partially hydrolyzed alkoxysilane, acid solid catalyst, water and reaction by-products;
(b) separating the volatile reaction by-products and water from the partially hydrolyzed silane by vacuum distillation in the presence of the solid acid catalyst to condense remaining alkoxysilane and thereby form silane diol having a low alkoxy concentration;
(c) adding an effective amount of solid magnesium oxide catalyst to neutralize the acid solid catalyst and to condense the silane diol to form a mixture containing neutralized, low molecular weight, linear, silanol-stopped polysiloxane;
(d) optionally adding an effective catalytic amount of solid calcium oxide catalyst to the mixture containing neutralized, low molecular weight, linear, silanol-stopped polysiloxane to condense the silanol-stopped polysiloxane and thereby increase the chain length of the polysiloxane; and
(e) separating the volatile by-products and solid catalysts from the low molecular weight, linear, silanol-stopped polysiloxane, whereby the polymer chain length varies according to the specific catalyst or catalyst combination, the silanolstopped polysiloxane having an average chain length of about 2.5 to about 4 siloxane units when magnesium oxide is used as catalyst, and the silanol-stopped polysiloxane having an average chain length of about 5 to about 6 siloxane units when calcium oxide is used as catalyst after magnesium oxide addition.

The reactivity and the stability of polysiloxanes vary significantly when chain length is increased from 2 to 6 siloxane units. If high reactivity is necessary or desired, shorter chains are preferred. When stability in handling is more important then the longer chain lengths are preferred.

The alpha, omega-siloxane diols having about 2 to about 6 siloxane units in chain length and prepared by the process of the present invention are useful as rubber processing aids, as a source of water in siloxane formulations and as an additive to modify RTV cure rates. The tetramethyldisiloxanediol is also useful in the synthesis of siloxane cyclics as described in U.S. Pat. No. 3,876,677.

HYDROLYSIS OF DIMETHYLDIMETHOXYSILANE IN THE PRESENCE OF ACID SOLID CATALYST TO MAKE STABILIZED CRYSTALLINE TETRAMETHYLDISILOXANEDIOL

In accordance with one aspect of the invention, there is provided a method of making stabilized, crystalline tetramethyldisiloxane diol comprising:
(a) mixing dimethyldimethoxysilane with a stoichiometric excess of water in the presence of an effective catalytic amount of solid acid catalyst for about 5 minutes to about 25 minutes at a temperature less than about 25° C. to form a partially hydrolyzed dimethyldimethoxysilane;
(b) distilling the reaction mixture in the presence of the acid catalyst at a temperature less than about 30° C. and at a pressure less than atmospheric pressure until volatile components are removed to substantially react the remaining alkoxy groups in the dimethylsiloxanediol;
(c) adding an effective catalytic amount of solid magnesium oxide catalyst to condense the dimethylsiloxanediol and thereby form a reaction mixture containing a mixture of siloxanediols having chain lengths of 2,3 and 4, condensation by-products and solid catalysts;
(d) filtering the reaction mixture to remove the solid catalysts from the filtrate;
(e) distilling the filtrate at a temperature of about 25° C. to about 65° C. at a pressure less than atmospheric pressure until volatile components are removed therefrom to produce an oil; and,
(f) cooling the oil to precipitate stable crystalline tetramethyldisiloxanediol and separating the crystalline product, preferably by filtration.

In a preferred embodiment, the mixture of dimethyldimethoxysilane, water and solid acid catalyst are vigorously mixed at about -10° C. to about 22° C., and the acid solid catalyst is an acid-activated clay used in an amount of about 0.5 to about 2.0 parts by weight per 100 parts by weight of dimethyldimethoxysilane. The solid magnesium oxide catalyst is preferably used in an amount between about 0.05 and 6.0 parts by weight per 1.0 part by weight of acid solid catalyst. Unless otherwise specified, the reaction conditions and amounts of reactants and catalysts are discussed above for the hydrolysis of dialkoxysilanes using acid solid catalysts as hydrolysis catalyst.

In a typical process, at 25° C. and after stripping volatile components from the hydrolysis reaction and after the magnesium oxide treatment, 54-55% of the product was tetramethyldisiloxanediol-1,3 which crystallized from the oil or fluid remaining after stripping (distillation). The unrecrystallized and stored product prepared by the hydrolysis of dimethyldimethoxysilane and stored for 2 months at room temperature, melted at 65°-66° C., essentially the same value found for the recrystallized compound reported in the literature at J. AM. CHEM. SOC., 75 2713 (1953). The stability of the crystalline tetramethyldisiloxanediol-1,3, to silanol condensation was unexpected because tetramethyldisiloxanediol prepared by prior art processes continues condensing with time as evidenced by a decrease in melting point and an increase in higher molecular weight contaminants.

HYDROLYSIS OF DIMETHYLDIMETHOXYSILANE TO MAKE CRYSTALLINE DIMETHYLDISILANOL

In another aspect of the present invention, there is provided a method of making crystalline dimethyldisilanol comprising:
(a) mixing neutral dimethyldimethoxysilane with a stoichiometric excess of water for about 5 minutes to about 25 minutes at a temperature less than about 5° C. in the presence of an effective catalytic amount of solid acid catalyst, said catalyst being previously treated to remove all soluble acidity;
(b) filtering the reaction mixture cold to form a cold filtrate;

(c) distilling the cold filtrate at a pressure less than atmospheric pressure until crystals of dimethyldisilanol form in the filtrate; and (d) isolating the dimethyldisilanol crystals from the filtrate.

The hydrolysis reaction is preferably carried out by vigorous mixing of the solid acid catalyst, the dimethyldimethoxysilane and water at less than 5° C. The preferred solid acid catalyst is a washed acid-activated clay present in an amount of about 0.5 to about 2.0 parts by weight per 100 parts by weight of dimethyldimethoxsilane. All soluble acidity in the solid acid catalyst, for example, acid-activated clay, may be removed by any conventional method. For example, the soluble acidity in the acid-activated clay is removed by boiling the clay with aliquots of deionized water and filtering until the clay no longer affects the pH of the water. The dimethyldimethoxysilane may also be neutralized, and in preferred embodiments it is neutralized before the initiation of the hydrolysis by any suitable means, for example, by stirring with basic material, such as, magnesium oxide followed by filtering. One commercial material which may be used to neutralize the dimethyldimethoxysilane is Maglite K, a trademark for magnesium oxide supplied by Merck and Co., Inc. The filtration and the distillation are preferably carried out at less than about 10° C., and volatile components are removed from the dimethyldisilanol crystals at less than about 10° C. at a pressure of about 5 mm Hg to about 15 mm Hg. Unless otherwise specified, reactants and reaction conditions are the same as those described above for other modes of the present invention. The crystalline product melts at about 92°-100° C., and was 79 weight percent dimethyldisilanol, the remainder being polysiloxanediols. It may be used as a rubber processing aid, or it may be used in the synthesis of siloxane cyclics. The product is reported in the literature at J. AM. CHEM. SOC., 75, 2713 (1953).

The following specific examples describe the catalytic hydrolysis processes and products of this invention. They are intended for illustrative purposes only and should not be construed as a limitation.

Although any type of magnesium oxide may be used as catalyst in the processes of the present invention, in most cases, a commercially available magnesium oxide identified as Maglite K (a trademark of Merck and Co., Inc.) was used. Maglite K magnesium oxide is a relatively inactive magnesium oxide having an iodine number of 30 maximum. The purity of the Maglite K is 94.6% magnesium oxide and the particle size is such that 99.7% of the magnesium oxide passes through a 325 mesh screen.

EXAMPLE 1

HYDROLYSIS OF DIMETHYLDIMETHOXYSILANE USING MAGNESIUM OXIDE HYDROLYSIS CATALYST

To 240 grams (2 moles) of dimethyldimethoxysilane was added a combined mixture of 162 grams (9 moles) of distilled water and 0.2 grams of magnesium oxide commercially available as Maglite K (a trademark of Merck and Co., Inc.), to form a 2 phase system. The 2 phase system was stirred vigorously at room temperature, and after the first 5 minutes of mixing, the mixture became homogeneous, and the temperature rose to 45° C. because of the exothermic reaction. The reaction mixture was allowed to cool to room temperature, and after about 3 hours, a new second phase formed as an emulsion. After 21.25 hours, the mixture was stripped on a rotoevaporator until all the volatile components were removed therefrom, and the mixture was then held at 60° C. and 23 mm Hg. pressure for 25 minutes. About 2 grams of diatomaceous earth identified commercially as CELITE (Trademark of Johns-Manville Products Corporation) and 0.5 gram of a porous colloidal aluminum silicate (clay) known commercially as Fuller's earth, were added to the oil, and the oil was filtered. The filtrate was a water-white liquid having a viscosity of 25.6 centistokes and a refractive index of 1.4071 at 20° C. An analysis of the filtrate showed that it contained 1.9 weight percent methoxy groups and 11.5 weight percent silanol groups. An analysis by gas chromatography showed no detectable cyclic siloxane compounds in the stripped (distilled) product, however, 6.1 grams of cyclic siloxanes having 3 siloxane units and 4 siloxane units in the molecule and representing 4% of the starting dimethyldimethoxysilane were found in the distillate. The high silanol content and low viscosity indicate that few or no high molecular weight liner siloxanes were present. The unfiltered yield of 140.2 grams corresponds to 91% of the theoretical yield, assuming a chain length of 3.4 monomer units having silanol terminal groups at 92% of the chain ends. The averages were calculated from the methoxy and the silanol content of the fluid (oil).

EXAMPLE 2

31.75 kilograms dimethyldimethoxysilane and 26 grams magnesium oxide identified commercially as Maglite K (Maglite is a Trademark of Merck & Co., Inc.) were charged to a 50 gallon glass reaction vessel equipped with a reflux condenser. After adding 21.55 kilograms water, the mixture was agitated strongly for 18 hours. The hydrolysis proceeded as described in Example 1. The mixture was heated to 50° C. and stripped under vacuum at 50° C. A total of 15.2 kilograms of methyl alcohol by-product and water were vacuum distilled without a column at 15 to 25 mm Hg pressure. After the stripping was complete, the pressure was maintained at 15 to 25 mm Hg, and the temperature was held at between 50° and 60° C. for 15 minutes to produce a stripped silanol-stopped dimethylpolysiloxane oil (fluid).

The filter aid, diatomaceous earth, commercially available under the trademark Celite 545, a trademark of Johns-Manville Corporation, was added to the stripped dimethylpolysiloxanediol, and the mixture was filtered. The yield was 18.6 kilograms, 88.6% of theoretical, of water-white polydimethylsiloxanediol oil. The viscosity was 29 centistokes at 25° C.; the refractive index was 1.4080; the silanol in weight percent was 10.2; and the weight percent methoxy was 1.3. Gas liquid chromatography showed 2.6 area percent polysiloxane cyclics. The average chain length and percent of methoxy capped ends, calculated from the gas liquid chromatography analysis, were 3.8 siloxane units and 6%, respectively.

EXAMPLES 3-8

Except as indicated below and in Table I, the procedure of Example 2 as followed for Examples 3 through 8 in Table I below. The amount of catalyst used in Examples 3 through 8 was the same as reported in Example 2 above. In all cases, except in Example 8, the hydrolysis catalyst was Maglite K, a magnesium oxide catalyst. In Example 8 the catalyst was 99.999% pure magnesium oxide from Aldrich Chemical Co. In Example 3 the filter aid was a mixture of diatomaceous earth and Fuller's earth as set forth in Example 1 above.

Table II shows that neither higher nor lower temperatures dramatically effect product properties. Example 13 shows that 2 moles water per mole of silane results in a reduced yield.

TABLE II

EXAMPLES OF HYDROLYSIS OF DIMETHYLDIMETHOXYSILANE USING MAGNESIUM OXIDE AS HYDROLYSIS CATALYST (EFFECT OF REACTION TEMPERATURE)

| EXAMPLE NO. | MOLES H$_2$O MOLES Me$_2$Si(OMe)$_2$ | REACTION TIME (HYDROLYSIS) | REACTION TEMPERATURE (HYDROLYSIS) | YIELD % | % CYCLICS (GLC AREA) | VISCOSITY AT 25° C. (CENTISTOKES) | CHAIN LENGTH | WEIGHT % —OH | WEIGHT % —OMe | % OF SILANOL END-CAPPING | REFRACTIVE INDEX AT 25° C. |
|---|---|---|---|---|---|---|---|---|---|---|---|
| 9(1) | 4 | 30 min. @ plus 10 min. @ | 50° C. 60° C. | 86 | 0 | 22.7 | 3.0 | 13.9 | 2.5 | 91 | 1.407 |
| 10 | 4 | 3 hrs. | 0° C. | — | 1.7 | — | 2.8 | 12.7 | 3.3 | 88 | — |
| 11 | 6 | 3 hrs. | 0° C. | — | 1.6 | — | 3.1 | 12.5 | 1.5 | 94 | — |
| 12 | 6 | 3 hrs. | 50° C. | 90 | 1.8 | — | 3.9 | 10.0 | 2.0 | 90 | — |
| 13 | 2 | ¾ hrs. | 56° C. | ~50 | — | 19.1 | — | — | — | — | — |

(1)The amount of catalyst in Example 1 was 1 part Maglite K/100 parts silane by weight silane. All other examples in Tables I and II used 0.08 parts MgO/100 parts by weight silane.

TABLE I

EXAMPLES OF HYDROLYSIS OF DIMETHYLDIMETHOXYSILANE USING MAGNESIUM OXIDE AS HYDROLYSIS CATALYST (EFFECTS OF REACTION TIME, WATER/DIMETHYLDIMETHOXYSILANE RATIO AND CATALYST SOURCE)

| EXAMPLE NO. | (1) MOLES H$_2$O MOLES SILANE | REACTION TIME (HYDROLYSIS) | (2) REACTION TEMP. (HYDROLYSIS) | YIELD % | % CYCLIC (By Area) | VISCOSITY (Centistokes) | CHAIN LENGTH | —OH wt. % | —O—Me wt. % | % OF SILANOL END-CAPPING | REFRACTIVE INDEX |
|---|---|---|---|---|---|---|---|---|---|---|---|
| 3 | 3.5 | 19.75 HRS. | ROOM | 87 | 0 | 23.4 | 3.4 | 11.4 | 2.2 | 90 | 1.4069 |
| 4 | 4 | 18 HRS. | ROOM | 91 | 0 | 24.8 | 3.5 | 11.1 | 1.9 | 91 | 1.4065 |
| 5 | 4 | 3 HRS. | 25° C. | 88 | 0 | — | 3.5 | 10.9 | 2.5 | 89 | — |
| 6 | 6 | 2.0 HRS. | ROOM | 87 | — | 29.0 | 2.9 | 12.9 | 2.3 | 91 | 1.4070 |
| 7 | 6 | 7 HRS. | ROOM | 90 | — | 30.3 | 2.9 | 13.5 | 1.9 | 93 | 1.4070 |
| 8(3) | 6 | 2.0 HRS. | ROOM | 82 | 0 | 31 | 3.5 | 11.7 | 1.2 | 95 | 1.4075 |

(1)The silane was dimethyldimethoxysilane. In all examples, 240 grams of dimethyldimethoxysilane was used.
(2)Temperature after dissipation of heat from exotherm.
(3)In example 8, magnesium oxide having 99.999% purity from Aldrich Chemical Co. was used in place of magnesium oxide supplied under the trademark Maglite K.

The Examples in Table I illustrate the effects of the variation of the reaction time, the ratio of moles of water to moles of silane used and type of magnesium oxide used on product yield and product properties. The data in Examples 3, 4 and 7 show that more water produces more complete hydrolysis as indicated by a higher percent of silanol endcapping. A comparison of the data of Examples 4 with 5 and 6 with 7 shows that longer reaction time results in both higher yields and more complete hydrolysis. The data for Examples 6 and 8 show that ultra pure, anhydrous magnesium hydroxide gives more hydrolysis, more condensation, and a slightly lower yield. The primary case of the yield loss with ultrapure magnesium oxide as catalyst was the formation of a larger amount of hexamethylcyclotrisiloxane by-product which was removed during the stripping step.

EXAMPLES 9-13

Except as indicated below and in Table II, the procedure of Example 2 was followed for Examples 10 through 13. In all cases, except Example 9, the amount of catalyst was 0.08 part magnesium oxide per 100 parts by weight of the silane. Moles of water per mole of dimethyldimethoxysilane, hydrolysis reaction time and temperature are shown in Table II below. The data in In Tables I and II, the reaction time is the time at which the dimethyldimethoxysilane, water and magnesium oxide hydrolysis catalyst are vigorously stirred or mixed, and the hydrolysis reaction temperature is the temperature at which the hydrolysis reaction is maintained after the heat provided to the reaction mixture by the exothermic reaction, ceases. Viscosity measurements were taken at 25° C., and refractive index was measured at 25° C.

EXAMPLE 14

Following the procedure of Example 2, 0.3 gram of calcium oxide hydrolysis catalyst replaced the magnesium oxide catalyst. The amount of calcium oxide catalyst was 0.13 grams per 100 grams dimethyldimethoxysilane. The hydrolysis was carried out using 6 moles of distilled water per mole of dimethyldimethoxysilane. The hydrolysis reaction time was 2 hours, and the hydrolysis reaction temperature was maintained at 25° C. after the exothermic reaction conditions of the mixture heated the mixture to 49° C. The product was stripped of volatile materials and unreacted water over a period of 2 hours and 15 minutes at a temperature of 54° C. and a pressure of 18 mm Hg. The yield of the silanol-stopped polysiloxane fluid was 85% of theoretical. As determined by gas-liquid chromatography, no cyclic siloxanes were present in the product, and the viscosity of the product at 25° C. was 32 centipoises. The refractive index of the clear product was 1.4074 after filtration using diatomaceous earth filter aid. The percent silanol was 6.0; the percent methoxy was 1.06; and the percent of terminal groups (as silanol) was 91. The calculated average chain length (based upon the gas-liquid chromatographic analysis) was 6.6.

EXAMPLE 15

Following the procedure of Example 2, 0.8 grams of barium oxide (0.33 parts by weight barium oxide per 100 parts by weight dimethyldimethoxysilane) was used as the hydrolysis catalyst in place of magnesium oxide. The hydrolysis of dimethyldimethoxysilane was carried out using 6 moles of water per mole of dimethyldimethoxysilane. The hydrolysis reaction was carried out for 2 hours at a temperature of 25° C. after the reaction mixture reached a peak of 46° C. from the heat produced by the exotherm. The reaction mixture was stripped for 1 hour at 66° C. and 18 mm Hg. pressure. The viscosity of the silanol-stopped dimethylpolysiloxane fluid was 18,000 centistokes at 25° C. The percent silanol, as determined by the Zerewitinoff Method (Analysis of Silicones, A. L. Smith, John Wiley & Sons, 1974, page 136), was 0.23.

From the data reported for Examples 1 through 16, it can be seen that the chain length varies relative to the specific hydrolysis catalyst used in the hydrolysis of the dimethyldimethoxysilane. When magnesium oxide is used as the hydrolysis catalyst, the average chain length is about 3 to about 4. When calcium oxide is used as the hydrolysis catalyst, the average chain length is about 5 or 6. When barium oxide is used as the hydrolysis catalyst, the viscosity is relatively high, indicative of a relatively high chain length. The actual chain length of the silanol-stopped dimethylpolysiloxane product produced by the method of the present invention using barium oxide as the hydrolysis catalyst was too high (>25 units) to be determined by the gas-liquid chromatographic method used for other products.

HYDROLYSIS OF DIMETHYLDIMETHOXYSILANE USING ACID TREATED CLAY AS THE SOLID ACID HYDROLYSIS CATALYST, MAGNESIUM OXIDE AS THE NEUTRALIZING AGENT AND CALCIUM OXIDE AS THE CONDENSATION CATALYST

EXAMPLE 16

The hydrolysis of dimethyldimethoxysilane was initiated by charging 243 grams (13.5 moles) deionized water and 2.0 grams of an acid-activated clay catalyst identified commercially as Filtrol 20 (Filtrol is a trademark of Filtrol Corporation) to a glass vessel equipped with a distillation column and a reflux condenser. The contents were agitated and cooled to between 15° C. and 20° C., and 360 grams (3.0 moles) of dimethyldimethoxysilane were rapidly added, the addition being complete in 30 seconds. The mixture was agitated vigorously for 6.5 minutes after the addition of the dimethyldimethoxysilane. The reaction was exothermic for about 2 minutes, reaching a maximum temperature of 39° C. After the 6.5 minute period of vigorous stirring, the mixture was vacuum distilled while maintaining the temperature between 35° C. and 40° C. The distillation was continued for 4 hours until the distillation just ceased at 40° C. and 20 mm Hg pressure.

When the vacuum distillation was started, the average chainlength was 1.3 siloxane units, and the percent of silanol endcapping was 93%. After 211 minutes, the chainlength was 3.0, and the percent of silanol endcapping was greater than 99%. The values for chainlength and percent of silanol endcapping were obtained by quenching and trimethylsilylating reaction aliquoes with an excess of bis-trimethylsilyltrifluoroacetamide, then analyzing the stable derivatives by gas-liquid chromatography.

Following the vacuum distillation, 1.0 gram of magnesium oxide, identified commercially as Maglite K, was added to the reaction mixture, and the mixture was stirred for 15 minutes. Then 1.0 gram of calcium oxide was added and the mixture was stirred an additional 15 minutes. The mixture was then transferred to a rotoevaporator and stripped for 30 minutes at 45° C. and 15 to about 20 mm Hg pressure, removing all volatile materials. A mixture of 0.36 grams of Fuller's earth and sufficient diatomaceous earth to form a filter pad were then added to the stripped fluid, and the mixture was filtered. After filtration, the basicity was less than 5 ppm KOH. In this example where 0.28 parts magnesium oxide per 100 parts dimethyldimethoxysilane and 0.28 parts calcium oxide per 100 parts dimethyldimethoxysilane were used, the terminal ends were 99.9%-OH; the chain length as 5.1; the —SiOH was 8.55 weight percent; the —SiOMe, that is, the methoxy groups upon the silane, was 0.01 weight percent; the amount of silane in the form of cyclic silanes was 2.5%; the yield was 88.0% of theoretical; and the viscosity at 25° C. was 34.6 centipoises.

EXAMPLES 17 AND 18

The procedure for Examples 17 and 18 was the same as that used in Example 16, except as indicated below and in Table III. The principal significant difference is the omission of the distillation column during the first distillation step following the hydrolysis. In the most preferred embodiment, the distillation column is used because about 4% better yield was obtained (88% in Example 16 as compared with 84% in Example 17), and because the percent of silanol endcapping is higher at a given cyclics level (Compare Example 16 with Example 23 in Table IV and Example 24 in Table V).

In Example 17, the mixture was filtered before MgO was added, and again before the vacuum distillation that follows CaO addition. Example 18 had a single extra filtration step, before the vacuum distillation following the CaO addition. These extra filtration steps did not measurably affect the products, properties or neutrality. The data for Examples 17 and 18 is shown in Table III below:

TABLE III

HYDROLYSIS OF DIMETHYLDIMETHOXYSILANE USING ACID ACTUATED CLAY AS THE SOLID ACID HYDROLYSIS CATALYST, MAGNESIUM OXIDE AS THE NEUTRALIZING AGENT AND CALCIUM OXIDE AS CONDENSATION CATALYST

| EXAMPLE NO. | MOLES H$_O$ MOLES Me$_2$Si(OMe)$_2$ | REACTION TIME (Min.) | STRIPPING TIME (Min.) | TEMP. (°C.) | FINAL PRESSURE (mm Hg) | YIELD % | % CYCLICS (GLC AREA) | VISCOSITY at 25° C. (CENTISTOKES) | CHAIN LENGTH | WEIGHT % —OH | WEIGHT % —OMe | % OF SILANOL ENDCAPPING |
| --- | --- | --- | --- | --- | --- | --- | --- | --- | --- | --- | --- | --- |
| 17 | 4.5 | 18 | 122 | 41 | 20 | 84 | 0.63 | — | 5.3 | 8.1 | 0.07 | 99.5 |
| 18 | 4.5 | 18 | 120 | 45 | 16 | — | 0.44 | 37 | 5.3 | 8.3 | 0.08 | 99.5 |

HYDROLYSES OF DIMETHYLDIMETHOXYSILANE USING ACID ACTIVATED CLAY AND MAGNESIUM OXIDE.

These examples use the general procedure described in Example 16 except the calcium oxide is omitted and only the magnesium oxide is used as a neutralizing and condensing agent. The amounts of acid activated clay, commercially available as Filtrol 20, and magnesium oxide varied and are given in Table IV below, but the different amounts did not affect the product properties. In examples 19-23 6 moles of water, or water and ice, per mole of dimethyldimethoxysilane were used with the magnesium oxide identified as Maglite K.

EXAMPLE 19

Example 19 represents a preferred embodiment of the invention for making a polydimethylsiloxanediol having an average chainlength of 3 to 4 siloxane units. The dimethyldimethoxysilane contained no measurable acid or base, as demonstrated by no change in color upon addition of an aliquote to a green tetrabromophenolphthaleinethylester indicator solution (J. A. Magnuson & W. P. Baillargeon, Anal. Chim. Acta., 32, 186 (1965).) The amount of acid clay catalyst identified as Filtrol 20 was determined previously to be the minimum amount necessary to initiate hydrolysis of neutral dimethyldimethoxysilane using a 6/1 molar ratio of water to silane.

The hydrolysis was initiated by the addition of 360 g of silane to 324 g deionized water and 2.0 g of acid activated clay identified as Filtrol 20. The reaction temperature was initially 14° C. and rose to 34° C. in 3 minutes. At 4 minutes the percent of silanol endcapping was 95.4, and the chainlength was 1.0. The hydrolysate was transferred to a rotoevaporator for distillation after 8 minutes.

After distilling for 2 hours, distillation had essentially stopped at 50° C. and 20 mm Hg. The average chainlength was 3.2, and % of silanol endcapping was more than 99.9%. The product was neutralized and condensed slightly by the addition of 12 g of magnesium oxide identified as Maglite K. The distillation was continued for an additional 32 minutes giving an average chainlength of 3.4 with greater than 99.9% silanol endcapping. Then 4 g of filter aid identified as Celite 545 was added, and the product was filtered giving 192.5 g of clear, colorless oil. This product was stable for more than 5 months. Product composition, refractive index and viscosity are given in Table IV.

EXAMPLE 20

This example illustrates the importance of stripping in the presence of an unneutralized acid activated clay, for example, Filtrol 20, if a high percent (>96%) of silanol endcapping is desired. In Example 20 the volatiles were stripped after the magnesium oxide was added. The final product was only 96.1% silanol endcapped, a value comparable to that obtained when magnesium oxide was used as hydrolysis catalyst in Examples 6, 7 and 8.

In Example 20, 240 g of dimethyldimethoxysilane was added slowly to 216 g of distilled water and 4.8 g of acid activated clay identified as Filtrol 20 over 44 minutes. Initial temperature was 15° C., and the maximum temperature was 21° C. After 2 hours of vigorous mixing, 3.2 g of magnesium oxide identified as Maglite K was added, and the mixing was continued for 10 minutes. The neutralized hydrolysate was then filtered, and the clear filtrate stripped on a thin film rotoevaporator for two hours to a final temperature of 42° C. and a final pressure of 31 mm Hg. After adding 4 g of a filter aid identified as Celite 545, the stripped product was filtered, giving 130.4 g of clear, colorless oil. Product properties are given in Table IV. Example 20 is an embodiment included to show the importance of the first distillation step in reducing alkoxy content.

EXAMPLE 21

Example 21 demonstrates the need for a neutralization step in solid acid catalyzed hydrolyses if the silane and the solid acid catalyst are not pretreated to remove soluble acid residues. Although such pretreatment of the solid acid catalyst and the silane is possible, it is a more complex procedure. It is the preferred mode when the monomeric dimethylsilanediol is the desired product, as in Example 29. Example 21, described below and in Table IV, also illustrates the detrimental effect of hydrolyzing for more than 5 to 15 minutes before beginning the first distillation step when alkoxy and silanol group condensation takes place.

In Example 21, hydrolysis was initiated by the addition of 240 g (2.0 moles) of dimethyldimethoxysilanes (5 to 15 ppm HCl) to 4.8 grams of acid activated clay and 12 moles of water consisting 163 g (9.1 moles) of distilled water and 53 g (2.9 moles) of ice. The addition, made with vigorous mixing, was complete in 30 seconds, and the exothermic hydrolysis increased the reaction temperature to a maximum of 36° C. after 27 seconds. At one minute, the percent of silanol endcapping was 94.5%, and the average chainlength was 1.1. The reaction mixture was then allowed to cool to 25° C., and stirring was continued for 120 minutes at which time the average chainlength was 2.1 siloxane units and the extent of silanol endcapping was 93%. The volatiles were removed by vacuum distillation using a condenser but no distillation column. After distilling for 126 minutes at 22+/−3° C., and reaching a final pressure of 4 mm Hg, the residue was filtered through diatomaceous earth, giving a product which was not stable and which condensed with the formation of water. As seen in Table IV, after the vacuum distillation the average chain-length was 2.7 and the percent of silanol endcapping expectedly, the unrecrystallized tetramethyldisiloxanediol is stable indefinitely at room temperature. The properties of the oil and crystalline mixed product of Examples 22 and 23 are included in Table IV.

TABLE IV

HYDROLYSIS OF DIMETHYLDIMETHOXYSILANE USING MgO AS NEUTRALIZING AGENT(1)

| EXAMPLE NO. | g FILTROL 20 100 g $Me_2Si(OMe)_2$ | % of $H_2O$ as ICE | g MgO 100 g $Me_2Si(OMe)_2$ | HYDROLYSIS Rxn Time (min.) | Temp(2) (°C.) | 1st STRIPPING Time | Final Temp (°C.) | Final Pressure (mm Hg) |
|---|---|---|---|---|---|---|---|---|
| 19 | 0.56 | 0 | 3.3 | 8 | 14 | 120 | 50 | 20 |
| 20 | 2.0 | 0 | 1.3 | 120 | 15 | 198(3) | 48 | 31 |
| 21 | 2.0 | 25 | —(4) | 120 | 0 | 126 | 25 | 5 |
| 22 | 0.22 | 56 | 1.4 | 12 | 0 | 94 | 30 | 9 |
| 23 | 0.22 | 56 | 1.4 | 10 | 0 | 122 | 27 | 16 |

| EXAMPLE NO. | YIELD (%) | % Si as CYCLICS | VISCOSITY at 25° C. (csts.) | CHAIN LENGTH | —OH wt % | —OMe wt % | % of Silanol Endcapping |
|---|---|---|---|---|---|---|---|
| 19 | 90 | 3.1 | 42 | 3.4 | 12.5 | 0.02 | 99.9 |
| 20 | 88 | — | 39 | 3.2 | 12.5 | 1.1 | 96.1 |
| 21 | —(4) | — | — | 2.7 | 15.0 | 0.5 | 98.2 |
| 22 | 93 | <1 | —(5) | 2.5 | 16.4 | 0.2 | 99.4 |
| 23 | — | <1 | —(5) | 2.5 | 16.3 | 0.3 | 98.9 |

(1)All of these examples use 6 moles of water, including ice, per mole of $Me_2Si(OMe)_2$.
(2)Temperature at which the hydrolysis was started.
(3)The MgO was added, and the reaction mixture was filtered before any of the volatiles were stripped.
(4)Hydrolysate was not neutralized and the product was not stable, condensing further and generating water on standing.
(5)Product was a mixture of crystals and oil.

had increased, but only to 98.2%. Thus, when low methoxy endcapping levels are desired, distillation should be started as soon as the dialkoxysilane has reacted which is generally from about a few seconds to 10 minuts of reaction.

EXAMPLES 22 & 23

A SYNTHESIS OF TETRAMETHYLDISOLOXANEDIOL

In these reactions the temperature during hydrolysis was kept below 25° C. and during vacuum distillation the temperature was maintained below 30° C. In the neutralization step, the Maglite K (magnesium oxide) was filtered out after only 1-2 minutes of contact with the product. As a result, the products were approximately 50% tetramethyldisiloxanediol, which crystallized readily from the mixed dimethylpolysiloxanediol product.

In both cases, the hydrolysis was initiated by the addition of 360 g (3 moles) of dimethyldimethoxy silane to 0.8 g Filtrol 20, (acid activated clay) and 18 moles of water, consisting of 143 g distilled water and 181 g ice. The procedure is the same as that of Example 26 except as indicated below and in Table IV.

The vacuum distillation, using a rotoevaporator was begun after just 10-12 minutes of hydrolysis and was continued for 1.5 hours at 25+/−5° C., reaching a final pressure of 6 mm Hg. The Maglite K (magnesium oxide) was added; the mixture was stirred for 1-2 minutes; several grams of diatomaceous earth (Celite 545) was added; and the solution was filtered. The clear filtrate was stripped a second time, for 50 minutes at 62+/−3° C., reaching a final pressure of 9 mm Hg. In Example 22, the residue was filtered out, giving 217 g of a clear oil. Gas chromatographic analysis of this oil showed that it was 54 mole % tetramethyldisiloxanediol. On cooling, 37 g of white, waxy crystals were collected. The crystals had a melting point of 65.0°-66.0° C. The published value for the melting point of the diol is 65.5°-66.0° C. (J. Am. Chem. Soc., 75 2713 (1963). Un-

EXAMPLES 24-28

HYDROLYSIS OF DIMETHYLDIMETHOXYSILANE USING ACID ACTIVATED CLAY CATALYST AND CALCIUM OXIDE AS NEUTRALIZING AGENT

Using the general procedure of Example 16 above except that the magnesium oxide was omitted and only calcium oxide was used in the process, 162 g (9 moles) of water and 0.8 gram of the solid acid catalyst were added to a glass vessel, and the mixture was cooled to 15°-18° C. Thereafter, 174 parts by weight of dimethyldimethoxysilane were added, and the hydrolysis reaction was carried out under the conditions shown in Table V below. Following the vigorous agitation during the time of the hydrolysis reaction, the reaction mixture was vacuum distilled without a distilling column at the conditions shown in Table V below. In examples 19 through 22, the mixture was distilled from the reaction vessel using a condenser but no distillation column. In Example 23, a rotoevaporator representative of a thin film distillation method, was used for the first step. After the distillate was removed, the product remaining was treated with 7.0 grams of calcium oxide. This was stirred at ambient temperature for 15 minutes and then distilled to a final pressure of about 25 mm Hg. and at a final temperature of 25° C. to 40° C., conditions which substantially removed all volatile materials and water. Diatomaceous earth was added to the product remaining after the distillate was stripped therefrom, and the mixture was filtered. The filtrate was analyzed by gas-liquid chromatography techniques, and the characteristics of the product are shown in Table V below for each Example.

Calcium oxide is used as the neutralization agent in Examples 24 through 28. Calcium oxide is a less preferred neutralization agent because the final product is slightly basic (about 100 ppm calcium hydroxide) despite careful removal of all solids. This residual basicity destabilizes the product which becomes hazy and filled with water droplets after standing several days. However, Examples 24 through 28 illustrate the relationship between the product properties, i.e. yield, percent of cyclic polysiloxane by-product and percent silanol endcapping and the reaction conditions of moles of water per mole of silane and the conditions of the first distillation step carried out in the presence of unneutralized acid activated clay catalyst (Filtrol 20).

The data of Examples 24 through 26 show that as the time and temperature of the first distillation step is increased, the degree of silanol endcapping also increases, but at the expense of yield. This trade-off is improved by using more water per mole of alkoxysilane, but molar ratios greater than 6 are less desirable since they would make the distillation step long and energy consuming. A more desirable method of improving the yield/% silanol endcapping tradeoff is to use a distillation column during the first distillation as described in Example 16.

Example 28 illustrates the detrimental effect of an excessively long and hot first distillation step. The distillation was continued at 50° C. for 72 minutes after no more distillate was formed. These conditions converted 22% of the alkoxysilane to cyclic polysiloxane by-products.

ture. Three different sets of crystals were obtained and were washed with several aliquots of warm hexane. A total of 2.8 grams (15% of theoretical yield) of 84 mole % pure dimethyldihydroxysilane were obtained. The product melted at 92° C. to 102° C.

While the present invention has been described in detail with particular reference to certain preferred embodiments thereof, it will be understood that variations and modifications can be affected within the spirit and scope of the invention.

What is claimed is:

1. A process for hydrolyzing alkoxysilanes comprising:
   (a) mixing an alkoxysilane having the general formula:

$(R'O)_a Si R_{4-a}$ wherein R is selected from the group consisting of alkyl, cycloalkyl, aryl, arylalkyl, haloalkyl, alkaryl, alkenyl, hydrogen and mixtures thereof; R' is alkyl; and a is an integer from 1 to 4; a stoichiometric excess of water and an effective catalytic amount of solid hydrolysis catalyst selected from the group consisting of a solid oxide of a Group IIa metal and solid acid catalyst to form a hydrolysis mixture of

TABLE V

HYDROLYSIS OF DIMETHYLDIMETHOXYSILANE USING FILTROL 20 ACID ACTIVATED CLAY AS SOLID ACID CATALYST AND CaO AS NEUTRALIZING AGENT

| EXAMPLE NO. | M WATER M SILANE | HYDROLYSIS REACTION TIME (min.) | FIRST STRIPPING | | | % of SILANOL END-CAPPING | CHAIN LENGTH | VISCOSITY at 25° C. | —OH (wt. %) | —OMe (wt. %) | % Si as CYCLICS | YIELD (%) |
|---|---|---|---|---|---|---|---|---|---|---|---|---|
| | | | TIME (min.) | *TEMP (°C.) | *PRESS. (mm Hg) | | | | | | | |
| 24 | 3 | 10 | 38 | 25 | 25 | 94.7 | 5.3 | 32 | 7.8 | 0.79 | 0.25 | 93 |
| 25 | 3 | 26 | 98 | 34 | 25 | 97.3 | 5.0 | 34 | 8.5 | 0.43 | 0.97 | 90 |
| 26 | 3 | 19 | 230 | 25 | 25 | 96.2 | 6.0 | — | 7.0 | 0.51 | 1.6 | 87 |
| 27 | 3 | 21 | 264 | 40 | 25 | 99.0 | 5.0 | — | 8.6 | 0.16 | 0.26 | 85 |
| 28 | 4.5 | 6 | 180 | 50 | 20 | 99.9 | 7.9 | 27 | 5.6 | 0.01 | 22.0 | 83 |

*Final Temperature and Final Pressure.

EXAMPLE 29

A SYNTHESIS OF DIMETHYLSILANEDIOL

The uncondensed diol, dimethylsilanediol, can be prepared if no acid, including the solid acid catalyst, is present during the first vacuum distillation step, and if the reagents for hydrolysis are rigorously neutral. The general method of Example 16 was modified as described below.

To neutralize dimethyldimethoxysilane, 120 grams (1 mole) of the silane were stirred with magnesium oxide and filtered, which removed residual chlorosilanes therein. The Filtrol 20 (acid activated clay) was boiled with deionized water and filtered 2 consecutive times to provide an acid activated clay having no soluble acid. Deionized water (108 grams or 6 moles) and 1.5 grams of the washed, acid activated clay, were combined and placed in a constant temperature bath held at −7° C. The 1 mole of dimethyldimethoxysilane treated as above, was added over a period of 1.5 minutes. The exothermic hydrolysis raised the temperature of the reaction to a maximum of 2° C. After stirring for 17 minutes, the reaction mixture was filtered cold and then vacuum distilled at a pressure of 5 mm Hg until crystals formed. The crystals were filtered and were further dried at 5 mm Hg pressure while held at a cold temperahydrolyzed product, reaction byproducts, hydrolysis catalyst and unreacted water;

(b) separating volatile by-products and unreacted reagents from the hydrolyzed product in the presence of the solid hydrolysis catalyst to form a devolatilized hydrolysis mixture, said separation being one which reduces the alkoxy content of the alkoxysilane;

(c) neutralizing the devolatilized hydrolysis mixture with a sufficient amount of neutralizing agent when the catalyst is a solid acid catalyst and optionally adding a suitable amount of condensation catalyst to increase the molecular weight of the hydrolysis product; and (d) separating the hydrolysis catalyst from the product.

2. The process of claim 1 wherein the solid acid catalyst is an acid activated clay and wherein the neutralizing agent is selected from the group consisting of magnesium oxide, calcium oxide and mixtures thereof.

3. The process of claim 1 wherein the neutralizing/condensation agent is the oxide of the Group IIa metal, and the hydrolysis mixture is hydrolyzed and condensed simultaneously with mixing the dialkoxysilane, water and solid oxide of a Group IIa metal to form a neutral hydrolysis mixture.

4. The process of claims 1 or 3 further comprising adding a filter aid to the hydrolysis mixture or neutral hydrolysis mixture and filtering the hydrolysis mixture or neutral hydrolysis mixture to remove solids therefrom.

5. The process of claims 1 or 3 further comprising filtering the hydrolysis mixture or the neutralized hydrolysis mixture to remove solids therefrom.

6. The process of claim 1 wherein the hydrolyzed product is separated from the hydrolysis mixture by stripping volatile reaction by-products and unreacted water from the hydrolysis mixture and thereafter filtering the solids from the stripped hydrolysis mixture.

7. The process of claim 1 comprising distilling the hydrolysis mixture to devolatilize the hydrolysis mixture in the presence of unneutralized solid acid catalyst whereby alkoxy groups from the alkoxysilanes are removed by condensation.

8. The process of claim 1 further comprising maintaining the mixture of dialkoxysilane, water and hydrolysis catalyst at a temperature of about −10° C. to about 60° C.

9. The process of claim 1 wherein the alkoxysilanes are dialkoxysilanes having the general formula:

(R)₂Si(OR')₂

10. A process for the catalytic hydrolysis of dialkoxysilanes comprising:
(a) mixing a dialkoxysilane with a stoichiometric excess of water in the presence of an effective catalytic amount of a solid Group IIa metal oxide catalyst to form a silanol-stopped polysiloxane product; and
(b) separating volatile reaction by-products, unreacted water and solids from the silanol-stopped polysiloxane product.

11. The process of claim 10 further comprising adding a filter aid to the silanol-stopped polysiloxane product and filtering the silanol-stopped polysiloxane product to separate the solids therefrom.

12. The process of claim 10 wherein the dialkoxysilane has the general formula:

(R)₂Si(OR')₂ wherein R is selected from the group consisting of alkyl, haloalkyl, cycloalkyl, aryl, alkenyl, aralkyl, alkaryl, hydrogen and mixtures thereof, and R' is alkyl.

13. The process of claim 12 wherein the dialkoxysilane is dimethyldimethoxysilane.

14. The process of claim 10 wherein at least 3 moles of water per mole of dialkoxysilane are vigorously mixed with the dialkoxysilane.

15. The process of claim 10 wherein the dialkoxysilane, water and metal oxide catalyst are vigorously mixed at a temperature of about 0° C. to about 60° C.

16. The process of claim 10 wherein the dialkoxysilane, water and metal oxide catalyst are vigorously mixed for about 10 minutes to about 24 hours.

17. The process of claim 10 wherein the metal oxide catalyst is selected from the group consisting of magnesium oxide, calcium oxide and barium oxide.

18. The process of claims 10 or 17 wherein the metal oxide catalyst comprises about 0.01 to about 10 parts by weight of Group IIa metal oxide catalyst per 100 parts by weight of dialkoxysilane.

19. The process of claims 10 or 17 wherein the metal oxide catalyst comprises about 0.08 to about 1.5 parts by weight of Group IIa metal oxide catalyst per 100 parts by weight of dialkoxysilane.

20. The process of claim 10 wherein the volatile reaction by-products and unreacted water are separated from the silanol-stopped polysiloxane product by distillation.

21. The process of claim 10 wherein the volatile reaction by-products and unreacted water are separated from the polysiloxane product by distillation, and thereafter solids are separated from the silanol-stopped polysiloxane product by filtration.

22. The process of claims 10, 11 or 21 further comprising subjecting the silanol-stopped polysiloxane product to reduced pressure at an elevated temperature.

23. The process of claims 10, 11 or 21 further comprising subjecting the silanol-stopped polysiloxane product to reduced pressure to complete the removal of volatile components.

24. A method for controlling the chain length of silanol-stopped polysiloxanes prepared by the catalytic hydrolysis of dialkoxysilanes comprising:
(a) mixing an effective catalytic amount of a Group IIa metal oxide catalyst selected from the class consisting of magnesium oxide, calcium oxide and barium oxide with a dialkoxysilane and a stoichiometric excess of water to form a silanol-stopped diorganopolysiloxane; and,
(b) separating volatile reaction by-products unreacted water and solids from the silanolstopped polysiloxane product, whereby the polymer chain length varies according to the specific metal oxide catalyst, the silanol-stopped polysiloxane having a shorter average chain length when magnesium oxide is used as catalyst, an intermediate average chain length when calcium oxide is used as catalyst and a longer average chain length when barium oxide is used as catalyst.

25. The method of claim 24 wherein the solids are separated from the silanol-stopped polysiloxane product by filtration.

26. The method of claim 24 further comprising adding a filter aid to the silanol-stopped polysiloxane product and filtering the silanol-stopped polysiloxane product to separate the solids therefrom.

27. The method of claim 24 wherein the volatile reaction by-products and unreacted water are separated from the silanol-stopped polysiloxane product by distillation.

28. The method of claim 24 wherein the volatile reaction by-products and unreacted water are separated from the polysiloxane product by distillation, and thereafter solids are separated from the silanol-stopped polysiloxane product by filtration.

29. The method of claims 24, 27 or 28 further comprising subjecting the product to reduced pressure at an elevated temperature to complete the removal of volatile components.

30. The method of claim 24 wherein the average chain length of the silanol-stopped polysiloxane product is about 2 to about 3 siloxane (—SiO—) units when magnesium oxide is used as catalyst.

31. The method of claim 24 wherein the average chain length of the silanol-stopped polysiloxane is about 4 to about 6 siloxane (—SiO—) units when calcium oxide is used as catalyst.

32. The method of claim 24 wherein the dialkoxysilane has the general formula:

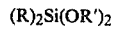

wherein R is selected from the group consisting of alkyl, cycloalkyl, aryl, alkenyl, aralkyl, alkaryl, hydrogen and mixtures thereof, and R' is alkyl.

33. The method of claims 24 and 32 wherein the dialkoxysilane is dimethyldimethoxysilane.

34. The method of claim 24 wherein at least 3 moles of water per mole of dialkoxysilane are vigorously mixed with the dialkoxysilane.

35. The method of claim 24 wherein the dialkoxysilane, water and metal oxide catalyst are vigorously mixed for about 10 minutes to about 24 hours.

36. The method of claim 24 wherein the dialkoxysilane, water and metal oxide catalyst are vigorously mixed at a temperature of about 0° C. to about 60° C.

37. The method of claim 24 wherein the catalyst comprises about 0.01 to about 10 parts by weight of the catalyst per 100 parts by weight of the dialkoxysilane.

38. A method for controlling the chain length of silanol-stopped dialkylpolysiloxanes prepared by the catalytic hydrolysis of dialkyldialkoxysilanes comprising:
(a) mixing a Group IIa metal oxide catalyst selected from the class consisting of magnesium oxide, calcium oxide and barium oxide with a dialkyldialkoxysilane and from about 3 to about 6 moles of water per mole of dialkyldialkoxysilane of about 0° C. to about 60° C., the catalyst being used in an amount from about 0.01 to about 1.5 parts by weight of metal oxide catalyst per 100 parts by weight of dialkyldialkoxysilane;
(b) distilling the reaction mixture after vigorously mixing for about 10 minutes to about 24 hours to separate volatile components and water from the silanol-stopped dialkylpolysiloxane product; and
(c) adding a solid filtering medium to the silanol-stopped dialkylpolysiloxane product and filtering said product, whereby the polymer chain length varies according to the specific metal oxide catalyst, the silanol-stopped dialkylpolysiloxane having an average chain length of about 2 to about 3 siloxane (—SiO—) units when magnesium oxide is used as a catalyst, an average chain length of about 4 to about 6 siloxane (—SiO—) units when calcium oxide is used as catalyst, and a longer average chain length when barium oxide is used as catalyst.

39. A process for the catalytic hydrolysis of dialkoxysilanes comprising:
(a) mixing an alkoxysilane with a stoichiometric excess of water in the presence of an effective catalytic amount of solid acid catalyst to initiate hydrolysis of the alkoxysilane and thereby form a mixture comprising partially hydrolyzed alkoxysilane, solid acid catalyst, water and reaction by-products;
(b) separating the volatile reaction byproducts and unreacted water from the partially hydrolyzed silane in the presence of the solid acid catalyst to condense alkoxy and silanol groups and thereby form silane diol having a low alkoxy concentration;
(c) neutralizing the silane diol with a suitable solid neutralizing agent thereby obtaining a neutralized, low molecular weight, linear, silanol-stopped polysiloxane and condensation by-products;
(d) optionally adding a solid condensation catalyst to the neutralized polysiloxane to increase the chain length of the polysiloxane; and
(e) separating the volatile by-products and solid catalyst from the low molecular weight, linear, silanol-stopped polysiloxane.

40. The process of claim 39 further comprising adding a filter aid and filtering the low molecular weight, linear, silanol-stopped polysiloxane to remove the acid solid catalyst.

41. The process of claim 39 further comprising filtering the low molecular weight, linear, silanol-stopped polysiloxane to separate the acid solid catalyst therefrom.

42. The process of claim 39 wherein the alkoxysilane has the general formula:

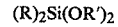

wherein R is selected from the group consisting of alkyl, haloalkyl, cycloalkyl, aryl alkenyl, aralkyl, alkaryl, hydrogen and mixtures thereof, and R' is alkyl.

43. The process of claim 42 wherein the dialkoxysilane is dimethyldimethoxysilane.

44. The process of claim 39 wherein at least 3 moles of water per mole of alkoxysilane are vigorously mixed with the alkoxysilane.

45. The process of claim 39 further comprising cooling the water and the acid solid catalyst to a temperature below ambient temperature and adding the alkoxysilane to the cooled aqueous medium.

46. The process of claim 45 further comprising vigorously mixing the alkoxysilane, acid solid catalyst and water while maintaining the temperature below ambient.

47. The process of claims 45 or 46 wherein the temperature is about −10° C. to about 60° C.

48. The process of claims 39, 45 or 46 wherein the mixture of alkoxysilane, water and solid acid catalyst are vigorously mixed for a sufficient length of time to form a single phase.

49. The process of claim 39 wherein the solid acid catalyst is an acid-activated clay.

50. The process of claims 39 or 49 wherein the solid acid catalyst is used in an amount of about 0.01 to about 20 parts by weight of catalyst per 100 parts by weight of alkoxysilane.

51. The process of claims 39 or 49 wherein the solid acid catalyst is used in an amount of about 0.5 to about 2.0 parts by weight of catalyst per 100 parts by weight of alkoxysilane.

52. The process of claim 39 wherein the volatile reaction by-products and unreacted water are separated from the partially hydrolyzed silane in the presence of the acid solid catalyst by distillation at a pressure of about 55 mm Hg to about 760 mm Hg.

53. The process of claims 39, 40, 41 or 52 further comprising subjecting the silanol-stopped, low molecular weight, linear polysiloxane to reduced pressure at a temperature between about 10° C. to about 60° C. to complete the removal of volatile components.

54. The process of claim 39 wherein the solid neutralizing agent is solid magnesium oxide, and the average chain length of the silanol-stopped, low molecular weight, linear polysiloxane is about 3 to about 4 siloxane (—SiO—) units.

55. The process of claims 39 or 54 wherein the amount of neutralizing agent is about 0.05 part by weight to about 6.0 parts by weight solid neutralizing agent per 1.0 part by weight of acid solid catalyst.

56. The process of claim 39 wherein the solid condensation catalyst is solid calcium oxide, and the average chain length of the silanol-stopped low molecular weight, linear polysiloxane is about 5 to about 6 siloxane (—SiO—) units.

57. The process of claims 39 or 56 wherein the amount of solid condensation catalyst is 0.05 part by weight to about 6.0 parts by weight condensation catalyst per 1.0 part by weight of acid solid catalyst.

58. A process for the catalytic hydrolysis of dialkyldialkoxysilanes comprising:
  (a) adding a dialkyldialkoxysilane to a mixture of about 3 to about 6 moles of water per mole of dialkyldialkoxysilane and about 0.5 to about 2.0 parts by weight of acid activated clay catalyst per 100 parts by weight of dialkyldialkoxysilane at a temperature of about −10° C. to about 25° C.;
  (b) mixing vigorously the mixture of step (a) at a temperature between about −10° C. to about 50° C. for the minimum time required to form a single phase to about 45 minutes to initiate hydrolysis of the dialkyldialkoxysilane and thereby form a mixture comprising partially hydrolyzed dialkylsilanes, acid solid catalyst, water and reaction by-products;
  (c) distilling the mixture at a temperature between about 15° C. and about 50° C. and at reduced pressure no less than about 15 mm Hg. pressure in the presence of the unneutralized solid acid catalyst to separate the volatile reaction by-products and water from the partially hydrolyzed dialkylsilane and to condense alkoxy and silanol groups, thereby forming low molecular weight, linear dialkylsilane diol product having a low alkoxy concentration;
  (d) adding about 0.05 to about 6.0 parts by weight solid magnesium oxide neutralizing agent and condensation catalyst per 1.0 part by weight of acid solid catalyst, and stirring for a sufficient time to evenly disperse the solid magnesium oxide, thereby obtaining a mixture containing neutralized, low molecular weight, linear, silanol-stopped dialkyl polysiloxane having an average chain length of about 3 to about 4 siloxane (—SiO—) units;
  (e) optionally adding up to about 6.0 parts by weight solid calcium oxide condensation catalyst per 1.0 part by weight of acid solid catalyst and stirring for a sufficient time to evenly disperse the solid calcium oxide in the mixture, thereby obtaining a mixture containing condensed, low molecular weight, linear, silanol-stopped dialkylpolysiloxane having an average chain length of about 5 to about 6 siloxane (—SiO—) units;
  (f) distilling the mixture containing low molecular weight, linear, silanol-stopped dialkylpolysiloxane until all volatile materials are removed; and
  (g) filtering the mixture remaining after removal of volatile materials to remove solid catalysts to obtain low molecular weight, linear, silanol-stopped dialkylpolysiloxane product.

59. The process of claim 58 wherein the dialkyldialkoxysilane is dimethyldimethoxysilane, and the product is dimethylpolysiloxanediol.

60. The process of claim 58 further comprising adding a filter aid to the mixture remaining after removal of the volatile materials to aid in the removal of the solid catalysts and to adjust the pH of the mixture.

61. A method for controlling the chain length of low molecular weight, linear, silanol-stopped polysiloxanes prepared by the catalytic hydrolysis of dialkoxysilanes comprising:
  (a) mixing a dialkoxysilane with a stoichiometric excess of water in the presence of an effective catalytic amount of solid acid catalyst to initiate hydrolysis of the dialkoxysilane and thereby form a mixture comprising partially hydrolyzed alkoxysilane, acid solid catalyst, water and reaction by-products;
  (b) separating the volatile reaction by-products and water from the partially hydrolyzed silane in the presence of the solid acid catalyst to condense alkoxy and silanol groups and thereby form silane diol having a low alkoxy concentration;
  (c) adding an effective amount of solid magnesium oxide catalyst to neutralize the acid solid catalyst and to condense the silane diol to form a mixture containing neutralized, low molecular weight, linear, silanol-stopped polysiloxane;
  (d) optionally adding an effective catalytic amount of solid calcium oxide catalyst to the mixture containing neutralized, low molecular weight, linear, silanol-stopped polysiloxane to condense the silanol-stopped polysiloxane and thereby increase the chain length of the polysiloxane; and
  (e) separating the volatile by-products and solid catalysts from the low molecular weight, linear, silanol-stopped polysiloxane, whereby the polymer chain length varies according to the specific catalyst or catalyst combination, the silanolstopped polysiloxane having an average chain length of about 2.5 to about 4 siloxane units when magnesium oxide is used as catalyst, and the silanol-stopped polysiloxane having an average chain length of about 5 to about 6 siloxane units when calcium oxide is used as catalyst after magnesium oxide is used as catalyst.

62. The method of claim 61 further comprising adding a filter aid and filtering the low molecular weight, linear polysiloxane to remove the solid catalyst.

63. The method of claim 61 wherein at least 3 moles of water per mole of dialkoxysilane are vigorously mixed with the dialkoxysilane.

64. The method of claim 61 wherein the mixture of dialkoxysilane, water and acid solid catalyst are vigorously mixed at about −10° C. to about 60° C. for a period of time sufficient to obtain a homogeneous mixture to about 45 minutes.

65. The method of claim 61 wherein the acid solid catalyst is an acid-activated clay used in an amount of about 0.5 to about 2.0 parts by weight of catalyst per 100 parts by weight of dialkoxysilane.

66. The method of claim 61 wherein the solid magnesium oxide is used in an amount between about 0.05 parts by weight to about 6.0 parts by weight per 1.0 part by weight of acid solid catalyst.

67. The method of claim 61 wherein the solid calcium oxide is used in an amount between about 0.05 part by weight to about 6.0 parts by weight per 1.0 part by weight of acid solid catalyst.

68. The process of claim 61 wherein volatile by-products and water are separated by vacuum distillation.

69. A method of making stabilized, crystalline tetramethyldisiloxanediol comprising:

(a) mixing dimethyldimethoxysilane with a stoichiometric excess of water in the presence of an effective catalytic amount of solid acid catalyst for about 5 minutes to about 25 minutes at a temperature less than about 25° C. to form a partially hydrolyzed dimethyldimethoxysilane;

(b) distilling the reaction mixture in the presence of the solid acid catalyst at a temperature less than about 30° C. and at a pressure less than atmospheric pressure until volatile components are removed to substantially react the remaining alkoxy groups in the dimethylsiloxanediol;

(c) adding an effective catalytic amount of solid magnesium oxide catalyst to condense the hydrolyzed dimethylsiloxanediol and thereby form a reaction mixture containing a mixture of siloxanediols having chain lengths of 1, 2, 3 and 4, condensation by-products and solid catalysts;

(d) filtering the reaction mixture to remove the solid catalysts from the filtrate;

(e) distilling the filtrate at a temperature of about 25° C. to about 65° C. at a pressure less than atmospheric pressure until volatile components are removed therefrom to produce an oil; and, (f) cooling the oil to crystalize stable tetramethyldisiloxanediol.

70. The method of claim 69 further comprising adding a filter aid to the reaction mixture prior to filtering the reaction mixture to remove the solid catalysts from the filtrate.

71. The method of claim 69 wherein at least 3.0 moles of water per mole of dimethyldimethoxysilane are vigorously mixed with the dimethyldimethoxysilane.

72. The method of claim 69 wherein the mixture of dimethyldimethoxysilane, water and acid solid catalyst are vigorously mixed at about −10° C. to about 25° C.

73. The method of claim 69 wherein the acid solid catalyst is an acid-activated clay used in an amount of about 0.5 to about 2.0 parts by weight per 100 parts by weight of dimethyldimethoxysilane.

74. The method of claim 69 wherein the solid magnesium oxide is used in an amount between about 0.05 part by weight and about 6.0 parts by weight per 1.0 part by weight of acid solid catalyst.

75. The method of claim 69 wherein the reaction mixture and the filtrate are distilled at a pressure of about 5 mm Hg to about 120 mm Hg.

76. A method of making crystalline dimethylsilanediol comprising:

(a) mixing neutral dimethyldimethoxysilane with a stoichiometric excess of water in the presence of an effective catalytic amount of solid acid catalyst free of soluble acid for about 5 minutes to about 25 minutes at a temperature less than about 5° C.;

(b) filtering the reaction mixture cold to form a cold filtrate;

(c) distilling the cold filtrate at a pressure less than atmospheric pressure until crystals of dimethyldisilanol form in the filtrate; and (d) isolating the dimethyldisilanol crystals from the filtrate.

77. The method of claim 76 wherein at least 3.0 moles of water per mole of dimethyldimethoxysilane are vigorously mixed with the dimethyldimethoxysilane.

78. The method of claim 76 wherein the mixture of dimethyldimethoxysilane, water and acid solid catalyst are vigorously mixed at about −15° C. to about +10° C.

79. The method of claim 76 wherein the acid solid catalyst is a neutralized acid-activated clay used in an amount of about 0.5 to about 2.0 parts by weight per 100 parts by weight of dimethyldimethoxysilane.

80. The method of claim 76 wherein the filtration and the distillation are carried out at less than about 10° C.

81. The method of claim 76 wherein the pressure less than atmospheric pressure is about 5 mm Hg to about 150 mm Hg.

* * * * *